United States Patent
Wittorff et al.

(10) Patent No.: US 12,128,138 B2
(45) Date of Patent: *Oct. 29, 2024

(54) MOUTHWASH FOR ORAL CARE BENEFITS

(71) Applicant: Fertin Pharma A/S, Vejle (DK)

(72) Inventors: Helle Wittorff, Vejle Ost (DK);
Christine Nøhr Pedersen, Aarhus C (DK)

(73) Assignee: Fertin Pharma A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/245,330

(22) Filed: Apr. 30, 2021

(65) Prior Publication Data
US 2021/0346263 A1    Nov. 11, 2021

(30) Foreign Application Priority Data

May 8, 2020   (DK) .............................. PA202070298

(51) Int. Cl.
| | | |
|---|---|---|
| *A61K 9/16* | (2006.01) | |
| *A61K 8/02* | (2006.01) | |
| *A61K 8/34* | (2006.01) | |
| *A61K 8/37* | (2006.01) | |
| *A61K 8/49* | (2006.01) | |
| *A61K 9/00* | (2006.01) | |
| *A61K 31/191* | (2006.01) | |
| *A61K 31/194* | (2006.01) | |
| *A61K 33/30* | (2006.01) | |
| *A61K 45/06* | (2006.01) | |
| *A61Q 11/00* | (2006.01) | |

(52) U.S. Cl.
CPC ............ *A61K 9/1623* (2013.01); *A61K 8/022* (2013.01); *A61K 8/0225* (2013.01); *A61K 8/345* (2013.01); *A61K 8/347* (2013.01); *A61K 8/37* (2013.01); *A61K 8/498* (2013.01); *A61K 9/0053* (2013.01); *A61K 31/191* (2013.01); *A61K 31/194* (2013.01); *A61K 33/30* (2013.01); *A61K 45/06* (2013.01); *A61Q 11/00* (2013.01); *A61K 2800/28* (2013.01); *A61K 2800/41* (2013.01); *A61K 2800/412* (2013.01); *A61K 2800/74* (2013.01); *A61K 2800/92* (2013.01)

(58) Field of Classification Search
CPC ........... A61Q 11/00; A61P 1/00; A61K 8/022; A61K 8/0225; A61K 8/345; A61K 8/347; A61K 8/37; A61K 8/498; A61K 8/27; A61K 8/34; A61K 8/4926; A61K 8/4973; A61K 8/922; A61K 9/1623; A61K 9/0053; A61K 9/0058; A61K 9/145; A61K 9/0056; A61K 31/191; A61K 31/194; A61K 31/045; A61K 31/047; A61K 31/05; A61K 31/09; A61K 31/135; A61K 31/137; A61K 31/167; A61K 31/192; A61K 31/352; A61K 31/4425; A61K 31/485; A61K 31/60; A61K 33/30; A61K 45/06; A61K 47/02; A61K 47/26; A61K 2800/28; A61K 2800/41; A61K 2800/412; A61K 2800/74; A61K 2800/92
See application file for complete search history.

(56) References Cited

U.S. PATENT DOCUMENTS

| | | | | |
|---|---|---|---|---|
| 5,536,526 | A * | 7/1996 | Virtanen .................. | C07H 3/02 426/660 |
| 2005/0260266 | A1* | 11/2005 | Gebreselassie .......... | A61K 8/11 424/468 |
| 2009/0172902 | A1* | 7/2009 | Cullup ............... | A46B 15/0055 401/16 |
| 2013/0149359 | A1 | 6/2013 | Sanders | |
| 2014/0314845 | A1 | 10/2014 | Yamanaka | |
| 2014/0345648 | A1 | 11/2014 | Abdalla | |
| 2016/0000695 | A1* | 1/2016 | Perez Davidi ......... | A61K 36/28 424/48 |
| 2016/0263170 | A1* | 9/2016 | Turner ................... | A61K 36/28 |
| 2018/0140521 | A1* | 5/2018 | Geonnotti ............ | A61K 9/2018 |

FOREIGN PATENT DOCUMENTS

| | | | | |
|---|---|---|---|---|
| WO | WO-9412150 A1 * | 6/1994 | .......... | A61K 38/164 |
| WO | WO200066171 | 11/2000 | | |
| WO | WO200582417 | 9/2005 | | |
| WO | WO-2007074472 A2 * | 7/2007 | .......... | A61K 31/167 |
| WO | WO2019219142 | 11/2019 | | |
| WO | WO2019219144 | 11/2019 | | |
| WO | WO2019219145 | 11/2019 | | |
| WO | WO2019219147 | 11/2019 | | |

* cited by examiner

*Primary Examiner* — Isaac Shomer
*Assistant Examiner* — Amanda Michelle Petritsch
(74) *Attorney, Agent, or Firm* — FORGE IP, PLLC

(57) ABSTRACT

A mouthwash and method for oral care benefits includes a swishable powder delivery system having a content of at least two types of sugar alcohol particles with different particle size distributions and one or more active ingredients, the powder delivery system being a dry and flowable population of particles suitable for resembling a liquid mouthwash by swishing the powder delivery system, thereby generating fluid in the oral cavity without adding water.

29 Claims, No Drawings

MOUTHWASH FOR ORAL CARE BENEFITS

FIELD OF THE INVENTION

The present invention relates to the field of mouthwashes suitable for cleansing and oral care benefits. In particular, the invention relates to a swishable powder delivery system for use as an alternative to liquid mouthwashes, and to a method of achieving oral care benefits.

BACKGROUND OF THE INVENTION

Traditionally, mouthwashes have been provided as liquid solutions intended for oral application by applying a portion of the liquid in the mouth whereafter the user starts swirling or gargling the liquid around in the oral cavity. In this way, the active solution of the mouthwash provides rinsing properties to the teeth and oral cavity in general. The user is instructed to avoid swallowing the mouthwash liquid during cleansing and usually also after cleansing has taken place by spitting the solution out after use.

Various different commercial products have been provided in the past. Common to these products is that they contain active ingredients dissolved in a liquid and are usually applied in bottles. In certain instances, the user is directly instructed to only apply a defined portion of the liquid, or the bottle is equipped with means for applying a defined portion of the liquid. In some other cases, it is the responsibility of the user to apply a correct portion of the liquid. Accordingly, the active ingredients contained in the liquid may not be applied in an appropriate defined amount, which may result in excess application of active ingredients.

Typically, it has been common practice to consider a liquid solution mouthwash as the only type of mouthwash of providing oral care benefits to the user in need thereof. The implication is that mouthwashes in bottles are delivered in all geographical locations with varying humidity, temperature and other conditions. In some geographical locations or for extreme local conditions, the active ingredients may be affected or otherwise influenced by ambient variations, such as temperature. Accordingly, the oral cleansing or rinsing effect of the liquid solution may be harmed in some instances, such as for vulnerable actives, and therefore the products may not achieve the marketed benefits or may even require application of a larger amount of the liquid solution in order to comply with the oral cleansing properties claimed. As a result, some active ingredients in the solution or the solvent may be applied in a higher amount than anticipated, which in turn may lead to harmful side effects.

Accordingly, there is a need in the art for mouthwash products that may contribute to a safer and less unpredictable application by a more accurate and precise administration of active ingredients for oral care benefits. In particular, it would be a benefit to only administer a concentration of active ingredients or an amount of active ingredients that may serve to comply with a more safe and effective usage of the active ingredients without the active ingredients being applied in excess amounts or in less effective amounts.

Likewise, there is a need in the art for products that may be more stable during storage and that may be more reliable upon use with respect to administration of active ingredients used in the mouthwash, expients used in the mouthwash, or solvents used in the mouthwash. In this respect, it would be a benefit with a mouthwash that may not be as easily affected by various extreme conditions occurring in some geographical locations or in some regions around the world.

Oral cleansing can be difficult or inconvenient at times, depending on the nature of the cleansing and the situation in which the cleansing must occur. Brushing, flossing, cleaning the tongue and gargling using a variety of devices and compositions are common oral care practices. However, the devices and compositions used in oral cleansing practices are less convenient to use away from home, where bathroom facilities might be scarce, unavailable, or unsanitary. For example, portable flossers can clean teeth on the go, but they are not discreet as well as not enjoyable to use, therefore consumers do not use them compliantly.

Also, with respect to these means for oral cleansing, there is a need in the prior art for mouthwash products that may serve to avoid the drawbacks of these products partly or completely, both in situations where these means may be less preferred or in situations where these means by replacement would provide increased efficiency.

As an alternative, oral tablets have been disclosed for administration of active pharmaceutical ingredients and active ingredients having health improving benefits.

Both in terms of convenience and compliance, oral tablets have certain benefits compared to other delivery vehicles for oral administration of active ingredients. Additional benefits include uniformity of content which is of particular importance for active pharmaceutical ingredients where lack of safety and appropriate delivery may become fatal in alleviating or treating medical conditions.

Oral tablets for gastrointestinal and or mucosal delivery of active ingredients are also commonly preferred with respect to securing an appropriate route of administration. Typically, such oral tablets are made by direct compression or compaction methods where a powder tablet material and an active ingredient are pressed into defined tablets with appropriate strength to provide a pharmacological effect to a patient in need thereof in medical formulations or to provide a health benefit for consumers in nutraceutical formulations.

In spite of the efforts and previous improvements of formulating oral tablets, hitherto known oral tablets are associated with various drawbacks. For instance, the time delay from administration of oral tablets to full efficacy of the active ingredient may inherently be delayed since the active ingredients are usually released over time from the oral tablet. This applies for instance when the tablet is designed for buccal absorption or gastrointestinal delivery. Different improved tablets have been provided, such as oral disintegrating tablets where the aim is to have the tablets disintegrate relatively fast. However, these tablets may only help but do not solve the issue of delay.

Additionally, convenience may be considerably compromised for certain consumers by formulating active ingredients in oral tablets. Here, aspects such as problems with swallowing tablets become critical, for instance for people with dry mouth and reduced saliva generation. Eventually, this may result in poor treatment for medical patients or poor health benefits for consumers of nutraceutical ingredients.

Particularly, only minor attention is given to benefits that may help obtaining release characteristics of active ingredients resulting in increased convenience and effectiveness. One of these release characteristics is increased generation of saliva. Increased generation of saliva and particularly an experience of increased saliva generation upon administration may for instance have some pronounced benefits for delivery of active ingredients to mucosal surfaces and teeth.

Furthermore, it is preferable that a formulation is provided that may also help in obtaining improved sensorial properties of active ingredient delivery. Here, important sensorial properties include mouthfeel, melting sensation, flavor sensation, salivation, cooling sensation, and off-note sensation associated with active ingredients. These properties are both relevant from a convenience perspective in oral administration, but certainly also in order to support an appropriate delivery of active ingredients and avoid adverse side effects of active ingredients. In particular mouthfeel is one of the more important sensorial properties of active ingredient delivery apart from efficacy.

One of the challenges with traditional mouthwash products and oral tablets as a delivery vehicle of active ingredients is that some active ingredients tend to be associated with off-notes during administration due to specific physiochemical properties. Taste masking challenges are more profound when a higher release of such active ingredients is required. If off-notes are the predominant sensation during administration, convenience may be affected and even more critically, delivery of such active ingredients may also be affected.

Hence, there is a need in the prior art for improved administration platforms that solve the above-referenced challenges and problems of the prior art. In particular, there is a need in the art for new platforms that support improved saliva generation, appropriate delivery of active ingredients combined with beneficial sensorial properties. Also, there is a need in the prior art for a mouthwash that may circumvent the drawbacks of an inaccurate administration of active ingredients in conventional liquid mouthwashes, and for mouthwash products that may withstand ambient conditions in certain geographical locations.

SUMMARY OF THE INVENTION

The present invention pertains to a new mouthwash product that is not in liquid form and is not in tablet form but contained in a swishable powder delivery system. This powder delivery system may be portioned in a flowpack. In particular, there is provided a swishable powder delivery system having a content of at least two types of sugar alcohol particles with different particle size distributions and one or more active ingredients, the powder delivery system being a dry and flowable population of particles suitable for resembling a liquid mouthwash by swishing said powder delivery system, thereby generating fluid in the oral cavity without adding water.

Generally, the present invention provides unexpected results by use of dry and flowable powder according to the invention as a mouthwash. The dry and flowable powder delivery system was seen by the inventors to provide surprisingly beneficial properties, resembling a liquid mouthwash by swishing said powder delivery system, thereby generating fluid in the oral cavity without adding water. Hence, by swishing the powder delivery system according to the invention, the system may replace liquid mouthwashes with the advantageous benefits compared to the aforementioned drawbacks of the prior art liquid mouthwash products.

For instance, the mouthwash according to the invention may contribute to an advantageous more accurate dosing of active ingredients, because the mouthwash in powder form may be stored in well-defined storage means, such as flowpacks, without there being a potential unprecise dosing seen for liquid mouthwashes. In turn, this advantage makes it possible to add active ingredients to the product and be sure that they are applied in a correct dose to the user.

Also, the relative standard deviation of active ingredients may be improved by applying separately dosing portions for the user according to the invention. In liquid mouthwashes, there may be some tendency to sedimentation of some active ingredients or uneven distribution of active ingredients with varying solubilities or ability to stay in suspension. The dry and flowable mouthwash according to the invention may circumvent these drawback of the prior art which provides a synergistic effect of the powder delivery system in view of the additional benefits provided according to the invention.

Likewise, the dry and flowable mouthwash according to the invention may be associated with an improved stability compared to liquid mouthwashes that may be subject to drawbacks, such as temperature problems or other ambient problems. Hence, the mouthwash according to the invention may be used in more extreme conditions and may be used as a more reliable and convenient system than liquid mouthwashes. The special composition of the powder delivery system may serve to generate increased saliva upon oral administration which may serve to resemble liquid mouthwashes, whereby liquid or water may be avoided.

In the present context, when the powder delivery system is mentioned to be "dry and flowable", the intended meaning is that the system behaves as a powder in the way that the water content is suitably low for a skilled person within powder technology to consider it "dry" for the purpose of a mouthwash and being able to "flow" for a skilled person within powder technology to consider it "flowable" for the purpose of a mouthwash. For instance, the system does not need to have a water content of 0.0% but may have a certain content of water to a degree that it behaves like a powder for the purpose of a mouthwash, such as less than 10.0% by weight, 8.0% by weight, 6.0% by weight, 4.0% by weight, 2.0% by weight water content, 1.5% by weight water, such as less than 1.0% by weight water content.

In terms of being "flowable", the powder delivery system according to the invention in some embodiments does not need to be "free-flowing". In some embodiments it is adequate that the powder is able to "flow" in the sense that certain agglomerations of particles are allowed and that not all types of particles in the powder delivery system is to be free-flowing. For instance, agglomeration to some extent during storage may be allowed, just that the powder may be gently handled to make the powder flowable to some extend or have flow properties. For the avoidance of doubt, a tablet is not considered "flowable" in the present context. Hence, the powder delivery system according to the invention is not a tablet or comprised in a tablet, such as a chewable tablet or orally disintegrating tablet according to the invention.

When reference is made to a "mouthwash" according to the invention, the intended meaning is the complete mouthwash product which may comprise a "mouthwash composition". However, a "mouthwash composition" may in some instances only be a part of the "mouthwash".

The meaning of "swishable" in the present context is to be understood as forcing either the powder delivery system around in the oral cavity or the liquid generated after a short period of time around in the oral cavity. The term "swishable" can also cover "gargling", "swirling" or "pushing around" or similar expressions. The idea is that the powder delivery system and the fluid generated is to be distributed in the oral cavity, both to oral mucosa, tongue and teeth in a way that it secures contact to the surfaces in the oral cavity. Upon "swishing", the idea is also that the portion of liquid generated is not to be swallowed during the operation, although a low amount is allowed to be swallowed while maintaining a major part of the saliva generated in the oral cavity in order to resemble a liquid mouthwash. Usually, the system is strong enough to avoid adding additional water.

However, water may be added to some extent but would not be required in order to deliver the advantages of the present invention.

In the present context, "fluid" or "fluid generation" or similar wording is to be understood in context with the invention as "saliva" or "saliva generation" as a result of the administration of the powder delivery system according to the invention. Hence, standard saliva generation is not the intended meaning, but excess saliva generation directly triggered by the powder delivery system is part of the context. When the population of particles is mentioned to resemble a liquid mouthwash, the intended meaning is that enough liquid is generated to attribute the same or improved oral care benefits as in liquid mouthwashes. The same amount of liquid as used in a liquid mouthwash is not needed according to the invention, just as long as the the amount of saliva generated would be manageable to be "swished". In some instances, however, the amount of saliva generated may be on the same level as by using a liquid mouthwash.

With respect to "oral care benefits" as used in the present context, it is noted that these effects would be understood by a person skilled in the art to cover certain benefits, such as stain removal benefits, plaque removal benefits, bad breath, whitening benefits, alleviation or treatment of gingivitis, or the like. These conditions may be addressed altogether in the mouthwash according to the invention, or one or more of the conditions may be addressed. Additionally, not only "oral care benefits" may be convered in the present context. Also, conditions in the throat may be addressed, and conditions in the gastrointestinal tract may be addressed by the present invention, such as if the dissolved mouthwash is swallowed.

In some embodiments of the invention, swishing said powder delivery system is characterised by forcing the powder delivery system around the oral cavity for a period of time.

In some embodiments of the invention, swishing said powder delivery system is characterised by forcing the powder delivery system around the oral cavity for at least 5 seconds. In some embodiments of the invention, swishing said powder delivery system is characterised by forcing the powder delivery system around the oral cavity for at least 10 seconds. In some embodiments of the invention, swishing said powder delivery system is characterised by forcing the powder delivery system around the oral cavity for at least 15 seconds. In some embodiments of the invention, swishing said powder delivery system is characterised by forcing the powder delivery system around the oral cavity for at least 20 seconds.

In some embodiments of the invention, at least a portion of the fluid generated by swishing said powder delivery system is forced around the oral cavity for a period of time.

In some embodiments of the invention, at least a portion of the saliva generated by swishing said powder delivery system is forced around the oral cavity for at least 10 seconds. In some embodiments of the invention, at least a portion of the saliva generated by swishing said powder delivery system is forced around the oral cavity for at least 20 seconds. In some embodiments of the invention, at least a portion of the saliva generated by swishing said powder delivery system is forced around the oral cavity for at least 30 seconds.

In some embodiments of the invention, at least a portion of the fluid generated by swishing said powder delivery system is forced around the oral cavity for a period of time prior to swallowing or spitting out said portion of fluid to provide an oral care benefit.

Surprisingly, the powder delivery system in some embodiments was able to dissolve relatively quickly after oral administration in the oral fluid generated upon administration. In some embodiments, the powder delivery system dissolve within 15 seconds. In some embodiments, the powder delivery system dissolve within 10 seconds. In some embodiments, the powder delivery system dissolve within 8 seconds. In some embodiments, the powder delivery system dissolve within 5 seconds.

In some embodiments of the invention, oral care benefits are obtained by swishing said powder delivery system and/or at least a portion of the fluid generated in the oral cavity for at least 10 seconds. In some embodiments of the invention, oral care benefits are obtained by swishing said powder delivery system and/or at least a portion of the fluid generated in the oral cavity for at least 10 seconds for at least 20 seconds. In some embodiments of the invention, oral care benefits are obtained by swishing said powder delivery system and/or at least a portion of the fluid generated in the oral cavity for at least 30 seconds.

In some embodiments of the invention, oral care benefits comprise bad breath, plaque, gingivitis, whitening or combinations of two or more thereof.

In some embodiments of the invention, the powder delivery system is a dry and flowable population of particles that is swished upon oral administration and generates fluid in the oral cavity without adding water, and thereby resembling a liquid mouthwash.

In some embodiments of the invention, the powder delivery system is a dry and flowable population of particles that is swished upon oral administration and generates fluid in the oral cavity, optionally adding water, and thereby resembling a liquid mouthwash.

In some embodiments of the invention, the powder delivery system is a dry and substantially free-flowing population of particles.

In some embodiments of the invention, the powder delivery system is a dry and free-flowing population of particles.

In some embodiments of the invention, at least one of the at least two types of sugar alcohol particles with different particle size distributions is substantially free-flowing.

In some embodiments of the invention, at least one of the at least two types of sugar alcohol particles with different particle size distributions is free-flowing.

In some embodiments of the invention, at least two of the at least two types of sugar alcohol particles with different particle size distributions are substantially free-flowing.

In some embodiments of the invention, at least two of the at least two types of sugar alcohol particles with different particle size distributions are free-flowing.

In some embodiments of the invention, all of the at least two types of sugar alcohol particles with different particle size distributions are substantially free-flowing.

In some embodiments of the invention, all of the at least two types of sugar alcohol particles with different particle size distributions are free-flowing.

In some embodiments of the invention, the Hausner ratio of the powder delivery system is between 1.00 and 1.59. Generally, a ratio above 1.59 is considered poor in the present context.

The Hausner ratio is known by a person skilled in the art to be the ratio between stamped powder (g/mL) and unstamped powder (g/mL) according to known methods. The ratio expresses the ratio between the bulk density of the stamped and unstamped powder. The Hausner ratio is usually categorized according to a compressibility index and expresses the flow character of a powder. Best flow character is obtained with a Hausner ratio of 1.00 and the higher the Hausner ratio, the less flowing is the powder.

In some embodiments of the invention, the Hausner ratio of the powder delivery system is between 1.00 and 1.45.

In some embodiments of the invention, the Hausner ratio of the powder delivery system is between 1.00 and 1.34.

In some embodiments of the invention, the Hausner ratio of the powder delivery system is less than 1.59, such as less than 1.45.

In some embodiments of the invention, the Hausner ratio of the powder delivery system is less than 1.34, such as less than 1.25.

In some embodiments of the invention, the mouthwash generates more than 1.5 mL fluid in the oral cavity within a period from 30 to 90 seconds from onset of swishing.

In some embodiments of the invention, the mouthwash generates more than 1.5 mL fluid in the oral cavity within a period from 90 to 180 seconds from onset of swishing.

In some embodiments of the invention, the mouthwash generates more than 1.5 mL fluid in the oral cavity within a period from 180 to 300 seconds from onset of swishing.

In some embodiments of the invention, the powder delivery system provides an improved cooling effect compared to a powder delivery system without at least one of the at least two types of sugar alcohol particles with different particle size distributions.

In some embodiments of the invention, the powder delivery system provides an improved watering effect compared to a powder delivery system without at least one of the at least two types of sugar alcohol particles with different particle size distributions.

In some embodiments of the invention, the powder delivery system provides an improved mouthfeel compared to a powder delivery system without at least one of the at least two types of sugar alcohol particles with different particle size distributions, the improved mouthfeel including at least one of less sandy mouthfeel, less dusty mouthfeel, less roughness mouthfeel, less sticky or improved texture.

Generally, the powder system of the present invention unlike traditional liquid mouthwashes or oral tablets may be associated with various benefits in terms of sensorial properties and various other properties, such as release properties. The powder system is designed to encompass a synergistic combination of different types of sugar alcohol particles. Combined, the different types of sugar alcohol particles serve to both deliver active ingredients with improved effect and to accommodate various sensorial benefits compared to conventional liquid mouthwashes or oral tablets, including improved mouthfeel. Also, the powder system is aimed to be superior compared to simpler and less intricate powder systems available for administration of active ingredients.

The inventors of the present invention did not expect that combining at least two types of sugar alcohol particles according to the invention would solve various of the prior art issues with liquid mouthwashes or oral tablets and more simple powder delivery systems. Such issues include improved saliva generation, appropriate delivery of active ingredients combined with beneficial sensorial properties.

Particularly, the present invention may help in obtaining a release characteristic of active ingredients that offers increased convenience and effectiveness. One of these release characteristics is increased generation of saliva. Increased saliva generation and particularly an experience of increased saliva generation upon administration may for instance have some pronounced benefits for delivery of active ingredients to mucosal surfaces.

Furthermore, the present invention may help in obtaining improved sensorial properties of active ingredient delivery. Here, important sensorial properties include mouthfeel, melting sensation, flavor sensation, salivation, cooling sensation, and off-note sensation associated with active ingredients or processing aids. Of particular concern is to provide a suitable mouthfeel in order to allow medical patients or consumers seeking health benefits a more accommodating treatment or alleviation of symptoms. Also, the present invention may help in improving taste-masking of off-notes during administration. The taste masking challenge is more profound when a higher release of such active ingredients are provided which is generally the case for the powder delivery system of the present invention.

In some embodiments of the invention, at least 95% by weight of said at least two types of sugar alcohol particles have a particle size below 500 microns.

In some embodiments of the invention, at least 50% by weight of said at least two types of sugar alcohol particles have a particle size below 250 microns.

In some embodiments of the invention, at least 60% by weight of said at least two types of sugar alcohol particles have a particle size below 250 microns.

In some embodiments of the invention, at least 20% by weight of said at least two types of sugar alcohol particles have a particle size below 100 microns.

In some embodiments of the invention, at least 30% by weight of said at least two types of sugar alcohol particles have a particle size below 100 microns.

In some embodiments of the invention, the population of particles includes at least 20% of one type of sugar alcohol particles having a particle size with more than 80% of the particles being below 250 microns and at least 20% of another type of sugar alcohol particles having a particle size with more than 80% of the particles being below 250 microns.

In some embodiments of the invention, the population of particles includes at least 20% of one type of sugar alcohol particles having a particle size with more than 80% of the particles being below 250 microns and at least 20% of another type of sugar alcohol particles having a particle size with more than 80% of the particles being below 300 microns.

In some embodiments of the invention, the population of particles includes at least 20% of one type of sugar alcohol particles having a particle size with more than 80% of the particles being below 250 microns and at least 20% of another type of sugar alcohol particles having a particle size with more than 80% of the particles being below 100 microns.

In some embodiments of the invention, the population of particles includes at least 20% of one type of sugar alcohol particles having a particle size with more than 80% of the particles being below 250 microns and at least 20% of another type of sugar alcohol particles having a particle size with more than 70% of the particles being below 100 microns.

In some embodiments of the invention, the population of particles includes at least two types of sugar alcohol particles comprising i) granulated sugar alcohol particles and ii) non-directly compressible (non-DC) sugar alcohol particles.

The combination of granulated sugar alcohol particles with non-directly compressible (non-DC) sugar alcohol particles according to the invention may provide advantages that conventional powder systems may not provide. One of such advantages is improved mouthfeel. Another is improved generation of saliva. According to the invention, the powder delivery system may turn into liquid relatively fast, i.e., liquefies relatively fast. Other advantages may include improved melting sensation, flavor sensation, cooling sensation, and off-note sensation associated with active ingredients.

In some embodiments of the invention, the population of particles includes at least two types of sugar alcohol particles comprising i) granulated sugar alcohol particles in an amount of at least 20% by weight of the population of particles and ii) non-directly compressible (non-DC) sugar alcohol particles in an amount of at least 20% by weight of the population of particles.

In some embodiments of the invention, the population of particles includes at least two types of sugar alcohol particles comprising i) granulated sugar alcohol particles and ii) non-directly compressible (non-DC) sugar alcohol particles having a particle size with more than 80% of the particles being below 500 microns.

In some embodiments of the invention, the population of particles includes at least two types of sugar alcohol particles comprising i) granulated sugar alcohol particles and ii) non-directly compressible (non-DC) sugar alcohol particles having a particle size with more than 50% of the particles being below 250 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles.

The combination of granulated sugar alcohol particles with directly compressible (DC) sugar alcohol particles that are not granulated sugar alcohol particles according to the invention may provide advantages that conventional powder systems may not provide. One of such advantages is improved mouthfeel. Another is improved cooling. Other advantages may include improved melting sensation, salivation, flavor sensation, and off-note sensation associated with active ingredients.

In some embodiments of the invention, the population of particles includes at least two types of sugar alcohol particles comprising i) granulated sugar alcohol particles in an amount of at least 20% by weight of the population of particles and iii) directly compressible (DC) sugar alcohol particles that are not granulated sugar alcohol particles in an amount of at least 20% by weight of the population of particles.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 80% of the particles being below 500 microns, such as more than 95% of the particles being below 500 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 80% of the particles being below 300 microns, such as more than 95% of the particles being below 300 microns.

In some embodiments of the invention, the population of particles includes at least two types of sugar alcohol particles comprising ii) non-directly compressible (non-DC) sugar alcohol particles and iii) directly compressible (DC) sugar alcohol particles that are not granulated sugar alcohol particles.

In some embodiments of the invention, the population of particles includes at least two types of sugar alcohol particles comprising ii) non-directly compressible (non-DC) sugar alcohol particles in an amount of at least 20% by weight of the population of particles and iii) directly compressible (DC) sugar alcohol particles that are not granulated sugar alcohol particles in an amount of at least 20% by weight of the population of particles.

In some embodiments of the invention, the population of particles includes at least two types of sugar alcohol particles comprising ii) non-directly compressible (non-DC) sugar alcohol particles having a particle size with more than 80% of the particles being below 500 microns and iii) directly compressible (DC) sugar alcohol particles that are not granulated sugar alcohol particles having a particle size with more than 80% of the particles being below 500 microns, such as more than 95% of the particles being below 500 microns.

In some embodiments of the invention, the population of particles includes at least two types of sugar alcohol particles comprising ii) non-directly compressible (non-DC) sugar alcohol particles having a particle size with more than 50% of the particles being below 250 microns and iii) directly compressible (DC) sugar alcohol particles that are not granulated sugar alcohol particles having a particle size with more than 80% of the particles being below 300 microns, such as more than 95% of the particles being below 300 microns.

In some embodiments of the invention, the population of particles includes at least three types of sugar alcohol particles comprising i) granulated sugar alcohol particles, ii) non-directly compressible (non-DC) sugar alcohol particles and iii) directly compressible (DC) sugar alcohol particles that are not granulated sugar alcohol particles.

The unique combination of granulated sugar alcohol particles with non-directly compressible (non-DC) sugar alcohol particles and directly compressible (non-DC) sugar alcohol particles that are not granulated sugar alcohol particles according to the invention may provide additional advantages that conventional powder systems may not provide. One of such advantages is improved mouthfeel. Another is improved generation of saliva. Yet another is improved cooling sensation. Other advantages may include improved melting sensation, flavor sensation, and off-note sensation associated with active ingredients.

The special property of "mouthfeel" involves various factors of the population of particles that combined contribute to the overall impression of mouthfeel. Objective criteria are set up for test panels that evaluate mouthfeel according to the invention. Among these criteria are elements such as roughness impression, texture impression and a sandy impression. The general aim of the invention may be to improve these elements to obtain an improved mouthfeel of the population of particles. Combined with improved release and improved sensations as mentioned above, the invention may ascertain synergistic benefits compared to conventional liquid mouthwashes, tablets or more simple powder delivery systems known in the art.

The granulated sugar alcohol particles according to the invention may in itself provide various advantages compared to more simple powder delivery systems known in the art. One of these advantages of the granulated sugar alcohol particles according to the invention is that they provide an improved mouthfeel despite having relatively large particle size. Without being bound to theory, it is believed that the surface morphology and/or chemical composition of granulated sugar alcohol particles according to the invention may also work in synergy with the non-directly compressible (non-DC) sugar alcohol particles and/or directly compressible (non-DC) sugar alcohol particles that are not granulated sugar alcohol particles according to the invention. Hence, advantages from all three types of particles may contribute to the overall benefits of the invention, and the combination may provide further unexpected synergistic properties of the powder delivery system of the invention.

In the present context, the term "types of particles" or similar wording, if nothing else is mentioned, is intended to mean that the particles are different in either surface morphology or chemical composition. For instance, two types of sugar alcohol particles may be granulated sugar alcohol particles and non-granulated sugar alcohol particles. In the broadest concept, the two types of sugar alcohol particles may both be granulated sugar alcohol particles, but different in either surface morphology or chemical composition. Typically, when non-directly compressible (non-DC) sugar alcohol particles are present, or when directly compressible (DC) sugar alcohol particles that are not granulated sugar alcohol particles are present, then the two types of particles are different sugar alcohols, such as granules of xylitol and erythritol respectively sorbitol. As such, the two types of particles may also comprise xylitol in granulated form and xylitol in non-granulated form.

In some embodiments of the invention, the granulated sugar alcohol particles i) are directly compressible (DC) sugar alcohol particles.

The term "DC sugar alcohol particles" refers to particles of direct compressible (DC) sugar alcohol. It is noted that the terms "DC sugar alcohol particles" and "DC particles" are used interchangeably. DC sugar alcohol particles may be obtained by granulating non-DC sugar alcohol with e.g. other sugar alcohols or binders for the purpose of obtaining so-called direct compressible particles (DC). This may be done in a process such as a wet granulation process, or in a dry granulation process. Also, granulation of non-DC sugar alcohol with water as binder is considered to result in DC sugar alcohol particles in the present context. Agglomeration of particles into a single particle is also within the intended meaning. Typically, DC sugar alcohol particles have a surface morphology with a rough surface morphology when seen in a scanning electron microscope. In the present context, "granulation" or "granulated" "or agglomeration" or similar wording is not intended to involve milling, comminuting, or grinding of larger crystalline particles into smaller particles.

The term "DC sugar alcohol particles that are not granulated sugar alcohol particles" refers to particles of direct compressible (DC) sugar alcohol, which have not been granulated but are DC by nature. Sorbitol particles is an example of such particles. In the present context, "granulation" or "granulated" or similar wording is not intended to involve milling, comminuting, or grinding of larger crystalline particles into smaller particles.

The term "non-DC sugar alcohol particles" refers to particles of non-directly compressible (non-DC) sugar alcohol. It is noted that the terms "non-DC sugar alcohol particles" and "non-DC particles" are used interchangeably. In the present context, the non-DC sugar alcohol particles refer to particles which have not been preprocessed by granulation with e.g. other sugar alcohols or binders for the purpose of obtaining so-called direct compressible particles (DC). Typically, non-DC sugar alcohol particles include particles obtained by crystallization, optionally followed by milling, comminuting, or grinding, which does not involve other sugar alcohols or binders. Thus, non-DC sugar alcohol particles are considered as particles consisting of non-DC sugar alcohol. However, some degree of impurity may be present. Hence, the particles may be considered as substantially consisting of non-DC sugar alcohol.

Likewise, non-DC sugar alcohol particles are considered as non-granulated sugar alcohol particles. Typically, non-DC sugar alcohol particles have a surface morphology with a smooth surface morphology when seen in a scanning electron microscope compared to DC sugar alcohol particles.

In some embodiments of the invention, non-DC sugar alcohol particles include crystalline sugar alcohol particles obtained by a crystallization process, optionally followed by milling, comminuting, or grinding, which does not involve other sugar alcohols or binders. In this context, "crystalline" is intended to mean that the individual particles are composed of a coherent crystal structure and not for instance a micro-crystalline structure where small crystalline particles are gathered to larger particles.

One advantage of the invention is a surprisingly strong saliva generation compared to conventional formulations. Particularly, the non-DC particles surprisingly induce a remarkable generation of saliva. Increased generation of saliva may have a huge impact on the delivery of the one or more active ingredients. Specifically, increased generation of saliva may increase exposure of the one or more active ingredients to mucosal surfaces and thereby contribute to an increased uptake in the oral mucosa. More specifically, when increased generation of saliva is commenced in a short time, the one or more active ingredients may relatively quickly be exposed to mucosal surfaces and thereby relatively quickly deliver a desired effect. Hence, a synergy between uptake of active ingredients and increased saliva generation may be seen according to the invention. Non-DC erythritol is an example of a sugar alcohol that may contribute significantly to increased generation of saliva.

One unexpected advantage over the prior art is that the saliva generation is surprisingly sustained even after a user has swallowed the bulk-portion of the non-DC sugar alcohols. This sustaining of the salivation generation may be advantageous in relation to many applications of the formulation ranging from mouthfeel, taste, flavor perception, etc.

In some embodiments of the invention, the population of particles includes at least three types of sugar alcohol particles comprising i) granulated sugar alcohol particles in an amount of at least 20% by weight of the population of particles, ii) non-directly compressible (non-DC) sugar alcohol particles in an amount of at least 20% by weight of the population of particles and iii) directly compressible (DC) sugar alcohol particles that are not granulated sugar alcohol particles in an amount of at least 20% by weight of the population of particles.

In some embodiments of the invention, the population of particles includes at least three types of sugar alcohol particles comprising i) granulated sugar alcohol particles, ii) non-directly compressible (non-DC) sugar alcohol particles having a particle size with more than 80% of the particles being below 250 microns and iii) directly compressible (DC) sugar alcohol particles that are not granulated sugar alcohol particles having a particle size with more than 80% of the particles being below 300 microns.

In one embodiment of the invention, the population of particles includes at least three types of sugar alcohol particles comprising i) non-directly compressible (non-DC) sugar alcohol particles having a particle size with more than 95% of the particles being below 250 microns, ii) directly compressible (DC) sugar alcohol particles that are not granulated sugar alcohol particles having a particle size with more than 70% of the particles being below 100 microns and iii) granulated sugar alcohol particles.

In some embodiments of the invention, the population of particles includes at least three types of sugar alcohol particles comprising i) granulated sugar alcohol particles, ii) non-directly compressible (non-DC) sugar alcohol particles having a particle size with more than 95% of the particles being below 250 microns and iii) directly compressible (DC) sugar alcohol particles that are not granulated sugar alcohol particles having a particle size with more than 80% of the particles being below 100 microns.

In some embodiments of the invention, the population of particles includes at least two types of sugar alcohol particles comprising i) granulated sugar alcohol particles and ii) non-directly compressible (non-DC) sugar alcohol particles having a particle size with more than 50% of the particles being below 400 microns.

In some embodiments of the invention, the population of particles includes at least two types of sugar alcohol particles comprising i) granulated sugar alcohol particles and ii) non-directly compressible (non-DC) sugar alcohol particles having a particle size with more than 80% of the particles being below 400 microns.

In some embodiments of the invention, the population of particles includes at least two types of sugar alcohol particles comprising i) granulated sugar alcohol particles and ii) non-directly compressible (non-DC) sugar alcohol particles having a particle size with more than 80% of the particles being below 250 microns.

In some embodiments of the invention, the population of particles includes at least two types of sugar alcohol particles comprising i) granulated sugar alcohol particles and ii) non-directly compressible (non-DC) sugar alcohol particles having a particle size with more than 95% of the particles being below 250 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 80% of the particles being below 500 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 95% of the particles being below 500 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 80% of the particles being below 400 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 95% of the particles being below 400 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 80% of the particles being below 300 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 95% of the particles being below 300 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 80% of the particles being below 100 microns.

In some embodiments of the invention, the population of particles includes at least two types of sugar alcohol particles comprising i) granulated sugar alcohol particles and iii) directly compressible (DC) sugar alcohol particles that are not granulated sugar alcohol particles having a particle size with more than 95% of the particles being below 100 microns.

In some embodiments of the invention, the population of particles includes at least three types of sugar alcohol particles comprising i) granulated sugar alcohol particles, ii) non-directly compressible (non-DC) sugar alcohol particles having a particle size with more than 80% of the particles being below 250 microns and iii) directly compressible (DC) sugar alcohol particles that are not granulated sugar alcohol particles having a particle size with more than 80% of the particles being below 300 microns.

In some embodiments of the invention, the population of particles includes at least three types of sugar alcohol particles comprising i) granulated sugar alcohol particles, ii) non-directly compressible (non-DC) sugar alcohol particles having a particle size with more than 95% of the particles being below 250 microns and iii) directly compressible (DC) sugar alcohol particles that are not granulated sugar alcohol particles having a particle size with more than 80% of the particles being below 100 microns.

In some embodiments of the invention, the population of particles includes at least two types of sugar alcohol particles comprising i) granulated sugar alcohol particles in an amount of at least 10% by weight of the population of particles.

In some embodiments of the invention, the population of particles includes at least two types of sugar alcohol particles comprising i) granulated sugar alcohol particles in an amount of at least 20% by weight of the population of particles.

In some embodiments of the invention, the population of particles includes at least two types of sugar alcohol particles comprising i) granulated sugar alcohol particles in an amount of at least 25% by weight of the population of particles.

In some embodiments of the invention, the population of particles includes at least two types of sugar alcohol particles comprising i) granulated sugar alcohol particles in an amount of at least 30% by weight of the population of particles.

In some embodiments of the invention, the population of particles includes at least two types of sugar alcohol particles comprising i) granulated sugar alcohol particles in an amount of at least 40% by weight of the population of particles.

In some embodiments of the invention, the population of particles includes at least two types of sugar alcohol particles comprising i) granulated sugar alcohol particles in an amount of at least 10% by weight of the population of particles and ii) non-directly compressible (non-DC) sugar alcohol particles in an amount of at least 10% by weight of the population of particles.

In some embodiments of the invention, the population of particles includes at least two types of sugar alcohol particles comprising i) granulated sugar alcohol particles in an amount of at least 20% by weight of the population of particles and ii) non-directly compressible (non-DC) sugar alcohol particles in an amount of at least 20% by weight of the population of particles.

In some embodiments of the invention, the population of particles includes at least two types of sugar alcohol particles comprising i) granulated sugar alcohol particles in an amount of at least 25% by weight of the population of particles and ii) non-directly compressible (non-DC) sugar alcohol particles in an amount of at least 25% by weight of the population of particles.

In some embodiments of the invention, the population of particles includes at least two types of sugar alcohol particles comprising i) granulated sugar alcohol particles in an amount of at least 30% by weight of the population of particles and ii) non-directly compressible (non-DC) sugar alcohol particles in an amount of at least 30% by weight of the population of particles.

In some embodiments of the invention, the population of particles includes at least two types of sugar alcohol particles comprising i) granulated sugar alcohol particles in an amount of at least 10% by weight of the population of particles and iii) directly compressible (DC) sugar alcohol particles that are not granulated sugar alcohol particles in an amount of at least 10% by weight of the population of particles.

In some embodiments of the invention, the population of particles includes at least two types of sugar alcohol particles comprising i) granulated sugar alcohol particles in an amount of at least 20% by weight of the population of particles and iii) directly compressible (DC) sugar alcohol particles that are not granulated sugar alcohol particles in an amount of at least 20% by weight of the population of particles.

In some embodiments of the invention, the population of particles includes at least two types of sugar alcohol particles comprising i) granulated sugar alcohol particles in an amount of at least 25% by weight of the population of particles and iii) directly compressible (DC) sugar alcohol particles that are not granulated sugar alcohol particles in an amount of at least 25% by weight of the population of particles.

In some embodiments of the invention, the population of particles includes at least three types of sugar alcohol particles comprising i) granulated sugar alcohol particles in an amount of at least 10% by weight of the population of particles, ii) non-directly compressible (non-DC) sugar alcohol particles in an amount of at least 10% by weight of the population of particles and iii) directly compressible (DC) sugar alcohol particles that are not granulated sugar alcohol particles in an amount of at least 10% by weight of the population of particles.

In some embodiments of the invention, the population of particles includes at least three types of sugar alcohol particles comprising i) granulated sugar alcohol particles in an amount of at least 20% by weight of the population of particles, ii) non-directly compressible (non-DC) sugar alcohol particles in an amount of at least 20% by weight of the population of particles and iii) directly compressible (DC) sugar alcohol particles that are not granulated sugar alcohol particles in an amount of at least 20% by weight of the population of particles.

In some embodiments of the invention, the population of particles includes at least three types of sugar alcohol particles comprising i) granulated sugar alcohol particles in an amount of at least 25% by weight of the population of particles, ii) non-directly compressible (non-DC) sugar alcohol particles in an amount of at least 25% by weight of the population of particles and iii) directly compressible (DC) sugar alcohol particles that are not granulated sugar alcohol particles in an amount of at least 25% by weight of the population of particles.

In some embodiments of the invention, at least 80% by weight of said population of particles have a particle size below 500 microns.

In some embodiments of the invention, at least 95% by weight of said population of particles have a particle size below 500 microns.

In some embodiments of the invention, at least 80% by weight of said population of particles have a particle size below 400 microns.

In some embodiments of the invention, at least 95% by weight of said population of particles have a particle size below 400 microns.

In one embodiment of the invention, at least 80% by weight of said population of particles have a particle size below 300 microns.

In one embodiment of the invention, at least 95% by weight of said population of particles have a particle size below 300 microns.

In some embodiments of the invention, at least 30% by weight of said population of particles have a particle size below 250 microns.

In some embodiments of the invention, at least 50% by weight of said population of particles have a particle size below 250 microns.

In some embodiments of the invention, at least 60% by weight of said population of particles have a particle size below 250 microns.

In some embodiments of the invention, at least 20% by weight of said population of particles have a particle size below 100 microns.

In some embodiments of the invention, at least 30% by weight of said population of particles have a particle size below 100 microns.

In some embodiments of the invention, the granulated sugar alcohol particles i) are wet granulated sugar alcohol particles or dry granulated sugar alcohol particles.

In some embodiments of the invention, the granulated sugar alcohol particles i) are dry granulated sugar alcohol particles.

In some embodiments of the invention, the granulated sugar alcohol particles i) comprise a binder, such as a carboxymethyl cellulose (CMC) binder. In an alternative embodiment, the binder is gummi *arabicum* or maltodextrine. Suitable binders include Gum Arabic, Methyl Cellulose, Liquid glucose, Tragacanth, Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

In some embodiments of the invention, the granulated sugar alcohol particles i) comprise a wet binder, such as water.

In some embodiments of the invention, the population of particles includes at least two types of sugar alcohol particles comprising i) granulated sugar alcohol particles selected from granulated particles of xylitol, maltitol, isomalt, mannitol, erythritol, lactitol or combinations thereof.

In some embodiments of the invention, the population of particles includes at least two types of sugar alcohol particles comprising i) granulated sugar alcohol particles selected from granulated particles of xylitol, maltitol, isomalt or combinations thereof.

In some embodiments of the invention, the population of particles includes at least two types of sugar alcohol particles comprising i) granulated particles of maltitol.

In some embodiments of the invention, the population of particles includes at least two types of sugar alcohol particles comprising i) granulated particles of xylitol.

In some embodiments of the invention, the population of particles includes at least two types of sugar alcohol particles comprising ii) non-directly compressible (non-DC) sugar alcohol particles selected from non-DC particles of xylitol, maltitol, isomalt, mannitol, erythritol, lactitol or combinations thereof.

In some embodiments of the invention, the population of particles includes at least two types of sugar alcohol particles comprising ii) non-directly compressible (non-DC) sugar alcohol particles selected from non-DC particles of xylitol, isomalt, mannitol, erythritol or combinations thereof.

In some embodiments of the invention, the population of particles includes at least two types of sugar alcohol particles comprising ii) non-directly compressible (non-DC) mannitol particles.

In some embodiments of the invention, the population of particles includes at least two types of sugar alcohol particles comprising ii) non-directly compressible (non-DC) erythritol particles.

In some embodiments of the invention, the population of particles includes at least two types of sugar alcohol particles comprising iii) directly compressible (DC) sugar alcohol particles that are not granulated sugar alcohol particles, and wherein the directly compressible (DC) sugar alcohol particles that are not granulated sugar alcohol particles iii) comprise sorbitol.

In some embodiments of the invention, the population of particles includes at least two types of sugar alcohol particles comprising iii) directly compressible (DC) sugar alcohol particles that are not granulated sugar alcohol particles, and wherein the directly compressible (DC) sugar alcohol particles that are not granulated sugar alcohol particles iii) is sorbitol.

In some embodiments of the invention, the granulated sugar alcohol particles i) are selected from granulated particles of xylitol, maltitol, isomalt, mannitol, erythritol or combinations thereof.

In some embodiments of the invention, the granulated sugar alcohol particles i) are selected from granulated particles of xylitol, maltitol, isomalt, erythritol or combinations thereof.

In some embodiments of the invention, the granulated sugar alcohol particles i) are selected from granulated particles of xylitol, maltitol, isomalt or combinations thereof.

In some embodiments of the invention, the granulated sugar alcohol particles i) comprise granulated particles of maltitol.

In some embodiments of the invention, the granulated sugar alcohol particles i) comprise granulated particles of xylitol.

In some embodiments of the invention, the granulated sugar alcohol particles i) are granulated particles of xylitol.

In some embodiments of the invention, more than 80% of the granulated sugar alcohol particles i) are within the range of 100 to 500 microns, such as more than 50% within a range of 100 to 400 microns. In one embodiment of the invention, more than 80% of the granulated sugar alcohol particles i) are within the range of 100 to 500 microns. In one embodiment of the invention, more than 80% of the granulated sugar alcohol particles i) are within the range of 100 to 400 microns. In one embodiment of the invention, more than 80% of the granulated sugar alcohol particles i) are within the range of 200 to 500 microns. In one embodiment of the invention, more than 80% of the granulated sugar alcohol particles i) are within the range of 200 to 400 microns.

In some embodiments of the invention, the granulated sugar alcohol particles i) provide the population of particles with free-flowing properties.

In some embodiments of the invention, the granulated sugar alcohol particles i) provide the other types of sugar alcohol particles in the population of particles with free-flowing properties.

In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles ii) are selected from non-DC particles of xylitol, maltitol, isomalt, mannitol, erythritol or combinations thereof.

In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles ii) are selected from non-DC particles of xylitol, isomalt, mannitol, erythritol or combinations thereof In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles ii) are selected from non-DC particles of mannitol, erythritol or combinations thereof.

In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles ii) comprise non-DC particles of mannitol.

In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles ii) comprise non-DC particles of erythritol.

In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles ii) are non-DC particles of erythritol.

In some embodiments of the invention, the population of particles includes at least two types of sugar alcohol particles comprising i) granulated sugar alcohol particles and ii) non-directly compressible (non-DC) sugar alcohol particles, and wherein the non-directly compressible (non-DC) sugar alcohol particles provide the population of particles with a salivation effect upon oral administration of the population of particles.

In some embodiments of the invention, the population of particles includes at least two types of sugar alcohol particles comprising i) granulated sugar alcohol particles and iii) directly compressible (DC) sugar alcohol particles that are not granulated sugar alcohol particles, and wherein the directly compressible (DC) sugar alcohol particles that are not granulated sugar alcohol particles iii) comprise sorbitol.

In some embodiments of the invention, the population of particles includes at least two types of sugar alcohol particles comprising i) granulated sugar alcohol particles and iii) directly compressible (DC) sugar alcohol particles that are not granulated sugar alcohol particles, and wherein the directly compressible (DC) sugar alcohol particles that are not granulated sugar alcohol particles iii) is sorbitol.

Sorbitol is an example of a sugar alcohol, which is considered DC grade, when provided as particles consisting of sorbitol, i.e., in its pure form. On the other hand, several other sugar alcohols are considered non-DC grade if providing them as particles consisting of the specific sugar alcohol. Therefore, such non-DC sugar alcohols are conventionally processed into DC grade sugar alcohols, e.g., by granulating them with e.g., a binder.

In some embodiments of the invention, the population of particles includes at least two types of sugar alcohol particles comprising i) granulated sugar alcohol particles and iii) directly compressible (DC) sugar alcohol particles that are not granulated sugar alcohol particles, and wherein the directly compressible (DC) sugar alcohol particles that are not granulated sugar alcohol particles iii) provide the population of particles with a cooling effect upon oral administration of the population of particles.

In some embodiments of the invention, the population of particles includes at least two types of sugar alcohol particles comprising i) granulated sugar alcohol particles and iii) directly compressible (DC) sugar alcohol particles that are not granulated sugar alcohol particles, and wherein the directly compressible (DC) sugar alcohol particles that are not granulated sugar alcohol particles iii) provide the population of particles with a cooling effect upon oral administration of the population of particles on the same level or more as xylitol based on weight percentage.

In some embodiments of the invention, the population of particles includes at least three types of sugar alcohol particles comprising i) granulated sugar alcohol particles, ii) non-directly compressible (non-DC) sugar alcohol particles and iii) directly compressible (DC) sugar alcohol particles that are not granulated sugar alcohol particles, and wherein the non-directly compressible (non-DC) sugar alcohol particles ii) is non-DC particles of erythritol and the directly compressible (DC) sugar alcohol particles that are not granulated sugar alcohol particles iii) is particles of sorbitol.

In some embodiments of the invention, the population of particles includes at least two types of sugar alcohol particles comprising i) granulated sugar alcohol particles and ii) non-directly compressible (non-DC) sugar alcohol particles in a weight ratio between i) and ii) of between 0.2 and 5.

In some embodiments of the invention, the population of particles includes at least two types of sugar alcohol particles comprising i) granulated sugar alcohol particles and ii) non-directly compressible (non-DC) sugar alcohol particles in a weight ratio between i) and ii) of between 0.3 and 4.

In some embodiments of the invention, the population of particles includes at least two types of sugar alcohol particles comprising i) granulated sugar alcohol particles and ii) non-directly compressible (non-DC) sugar alcohol particles in a weight ratio between i) and ii) of between 0.5 and 3.

In some embodiments of the invention, the population of particles includes at least two types of sugar alcohol particles comprising i) granulated sugar alcohol particles and iii) directly compressible (DC) sugar alcohol particles that are not granulated sugar alcohol particles in a weight ratio between i) and iii) of between 0.2 and 5.

In some embodiments of the invention, the population of particles includes at least two types of sugar alcohol particles comprising i) granulated sugar alcohol particles and iii) directly compressible (DC) sugar alcohol particles that are not granulated sugar alcohol particles in a weight ratio between i) and iii) of between 0.3 and 4.

In some embodiments of the invention, the population of particles includes at least two types of sugar alcohol particles comprising i) granulated sugar alcohol particles and iii) directly compressible (DC) sugar alcohol particles that are not granulated sugar alcohol particles in a weight ratio between i) and iii) of between 0.5 and 3.

In some embodiments of the invention, the population of particles includes at least two types of sugar alcohol particles comprising ii) non-directly compressible (non-DC) sugar alcohol particles and iii) directly compressible (DC) sugar alcohol particles that are not granulated sugar alcohol particles in a weight ratio between ii) and iii) of between 0.2 and 5.

In some embodiments of the invention, the population of particles includes at least two types of sugar alcohol particles comprising ii) non-directly compressible (non-DC) sugar alcohol particles and iii) directly compressible (DC) sugar alcohol particles that are not granulated sugar alcohol particles in a weight ratio between ii) and iii) of between 0.3 and 4.

In some embodiments of the invention, the population of particles includes at least two types of sugar alcohol particles comprising ii) non-directly compressible (non-DC) sugar alcohol particles and iii) directly compressible (DC) sugar alcohol particles that are not granulated sugar alcohol particles in a weight ratio between ii) and iii) of between 0.5 and 3.

In some embodiments of the invention, the active ingredient comprises acetaminophen. In some embodiments of the invention, the active ingredient comprises ibuprofen. In some embodiments of the invention, the active ingredient comprises phenylephrine. In some embodiments of the invention, the active ingredient comprises dextrometorphan. In some embodiments of the invention, the active ingredient comprises guaifenesin. In some embodiments of the invention, the active ingredient comprises diphenhydramine. In some embodiments of the invention, the active ingredient comprises acetaminophen, phenylephrine, and dextromethorphan. In some embodiments of the invention, the active ingredient comprises acetaminophen, phenylephrine, dextromethorphan, and guaifenesin. In one embodiment of the invention, the active ingredient comprises an active pharmaceutical ingredient.

In one embodiment of the invention, the active ingredient comprises an active nutraceutical ingredient. In one embodiment of the invention, the active ingredient comprises a dietary supplement. In one embodiment of the invention, the active ingredient comprises zinc citrate.

In one embodiment of the invention, the active ingredient comprises oral care agents. In one embodiment of the invention, the active ingredient comprises oral care agents including one or more probiotic agents.

In one embodiment of the invention, the active ingredient comprises oral care agents including zinc salts, such as zinc acetate or zinc gluconate. In one embodiment of the invention, the active ingredient comprises zinc acetate. In one embodiment of the invention, the active ingredient comprises zinc gluconate.

In one embodiment of the invention, the active ingredient comprises oral care agents for oral care benefits including bad breath, plaque, gingivitis, whitening, or combinations of two or more thereof. In one embodiment of the invention, the active ingredient comprises oral care agents for oral care benefits including one or more probiotic agents.

In one embodiment of the invention, the active ingredient comprises anti-septics. In one embodiment of the invention, the active ingredient comprises anti-septics including cetyl pyridinium chloride (CPC). In one embodiment of the invention, the active ingredient comprises anti-septics including essential oils. In one embodiment of the invention, the active ingredient comprises anti-septics including essential oils selected from the group consisting of menthol, methyl salicylate, cineole, thymol, and any combination thereof. In one embodiment of the invention, the essential oils include menthol, methyl salicylate, cineole, and thymol.

In one embodiment of the invention, the mouthwash further comprising one or more flavoring agents.

In one embodiment of the invention, the mouthwash further comprising one or more high-intensity sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural high sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another component such as a resinous compound.

Usage level of the high intensity sweetener will vary considerably and will depend on factors such as potency of the sweetener, rate of release, desired sweetness of the product, level and type of flavor used and cost considerations. Thus, the active level of high intensity sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the formulation.

The amount of flavor may e.g. be from 0.1 to about 10% by weight of the formulation, such as 0.1 to about 6% by weight of the formulation.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), chili, cinnamon redhots, cotton candy, circus cotton candy, clove, coconut, coffee, clear coffee, double chocolate, energy cow, ginger, glutamate, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

In some embodiments of the invention, the flavor is a powder flavor.

In some embodiments of the invention, the mouthwash further comprising at least one dissolution modifier selected from the group consisting of acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof.

In some embodiments of the invention, the at least one dissolution modifier is selected from the group consisting of sodium alginate, calcium polycarbophil, xanthan gum and mixtures thereof.

In some embodiments of the invention, the mouthwash further comprising at least one viscolising agent that when hydrated forms a gel having positive surface electrical charge and at least one viscolising agent that when hydrated forms a gel having negative surface electrical charge.

In some embodiments of the invention, the mouthwash further comprising abrasives, such as calcium carbonate and/or talc. In one embodiment of the invention, the mouthwash further comprising calcium carbonate. In one embodiment of the invention, the mouthwash further comprising talc.

In some embodiments of the invention, the mouthwash further comprising flow promoting agents. In some embodiments of the invention, the mouthwash further comprising silicon dioxide as a flow promoting agent. In some embodiments of the invention, the mouthwash further comprising rice hulls as a flow promoting agent. In some embodiments of the invention, the mouthwash further comprising cellulosic agents as flow promoting agents, such as Jelucel. In some embodiments of the invention the flow promoting agent is applied in an amount of less than 2.0% by weight of the mouthwash, such as less than 1.5% by weight, such as below 1.0% by weight.

In some embodiments of the invention, the mouthwash further comprising an effervescence system. In one embodiment of the invention, the mouthwash further comprising an effervescence system of a base and an acid.

In some embodiments of the invention, the mouthwash is a dose of about 0.5 to 5.0 g. In some embodiments of the invention, the mouthwash is a dosis of about 0.5 to 4.0 g. In some embodiments of the invention, the mouthwash is a dosis of about 1.0 to 3.0 g. In some embodiments of the invention, the powder mixture is a dosis of about 1.0 to 2.0 g.

In some embodiments of the invention, the population of particles includes gum base particles. In one embodiment of the invention, the population of particles includes chewing gum particles.

In some embodiments of the invention, the mouthwash is provided in a flowpack comprising an outer package material enclosing the population of particles and the one or more active ingredients.

In some embodiments of the invention, the mouthwash is provided in a flowpack comprising an outer aluminium package material enclosing the population of particles and the one or more active ingredients.

In some embodiments of the invention, the mouthwash is provided in a flowpack comprising an outer oxygen impermeable package material enclosing the population of particles and the one or more active ingredients.

In some embodiments of the invention, the population of particles is administered directly in the mouth.

In some embodiments of the invention, the population of particles is poured into water and the water is administered in the mouth.

In some embodiments of the invention, the population of particles is poured into water and the water is administered in the mouth.

In some embodiments of the invention, the population of particles is at least partially dissolved in water and the solution or dispersion is administered in the mouth.

In some embodiments of the invention, the mouthwash is for use in improving saliva generation.

In some embodiments of the invention, the mouthwash is for for use in the administration of active ingredients.

In some embodiments of the invention, the mouthwash is for use in the alleviation or treatment of xerostomia.

In some embodiments of the invention, the mouthwash is for use in alleviation or treatment of dysphagia.

In some embodiments of the invention, the mouthwash further comprising an effervescence system. In some embodiments of the invention, the mouthwash further comprising an effervescence system of a base and an acid. In one embodiment of the invention, the mouthwash further comprising an effervescence system of a base and an organic acid. In one embodiment of the invention, the mouthwash further comprising an effervescence system of a carbonate base and an organic acid.

In one aspect of the invention, there is provided a flowpack for oral delivery of active ingredients, the flow pack comprising an outer package material enclosing a swishable powder delivery system having a content of at least two types of sugar alcohol particles with different particle size distributions and one or more active ingredients, the powder delivery system being a dry and flowable population of particles suitable for resembling a liquid mouthwash by swishing said powder delivery system, thereby generating fluid in the oral cavity without adding water.

In this aspect, the flowpack comprises a swishable powder delivery system according to any one of the preceding embodiments.

In some embodiments of the invention, there is provided use of a mouthwash according to any of the preceding embodiments as a powder delivery system for improving saliva generation.

In some embodiments of the invention, there is provided use of a mouthwash according to any of the preceding embodiments as a powder delivery system for administration of active ingredients.

In some embodiments of the invention, there is provided use of a mouthwash according to any of the preceding embodiments as a powder delivery system for oral care benefits.

In some embodiments of the invention, there is provided use of a mouthwash according to any of the preceding embodiments as a powder delivery system for toothpaste.

In some embodiments of the invention, the flow pack may comprise a population of particles, an outer package material enclosing the population of particles, and one or more active ingredients, according to embodiments of the invention.

In some embodiments of the invention, there is provided a flowpack as a powder delivery system for improving saliva generation. Once the powder delivery system is introduced into the mouth according to this aspect of the invention, saliva may be generated to a higher degree than by using conventional types of sugar alcohol particles.

In some embodiments of the invention, there is provided a flowpack as a powder delivery system for administration of active ingredients.

In some embodiments of the invention, there is provided a flowpack as a powder delivery system for a mouthwash.

In some embodiments of the invention, the powder delivery system generates saliva and the user may force at least a portion of the saliva generated around the oral cavity, for example, by swishing, rinsing, washing, etc., to provide an oral care benefit.

In some embodiments of the invention, there is provided a flowpack as a powder delivery system for a toothpaste. In this aspect of the present invention, the powder delivery system generates saliva and the user may force at least a portion of the saliva generated around the oral cavity, for example, by swishing, rinsing, washing, etc., to provide a tooth paste cleaning benefit.

In some embodiments of the invention, there is provided a method of achieving oral care benefits, comprising the steps of:
  a) providing a swishable powder delivery system having a content of at least two types of sugar alcohol particles with different particle size distributions and one or more active ingredients, the powder delivery system being a dry and flowable population of particles, optionally provided in an outer flowpack material,
  b) resembling a liquid mouthwash by swishing said powder delivery system, thereby generating fluid in the oral cavity without adding water.

In some embodiments of the invention, there is provided a method of achieving oral care benefits, comprising the steps of:
  a) providing a swishable powder delivery system having a content of at least two types of sugar alcohol particles with different particle size distributions and one or more active ingredients, the powder delivery system being a dry and flowable population of particles, optionally provided in an outer flowpack material,
  b) subjecting the swishable powder delivery system into water, thereby obtaining an at least partly dissolved swishable powder delivery system, and
  c) swishing the at least partly dissolved swishable powder delivery system, thereby generating fluid in the oral cavity.

In one embodiment of the invention, the method comprises a swishable powder delivery system according to any one of the preceding embodiments.

DETAILED DESCRIPTION

Accordingly, the present invention provides a mouthwash for oral care benefits comprising a swishable powder delivery system having a content of at least two types of sugar alcohol particles with different particle size distributions and one or more active ingredients, the powder delivery system being a dry and flowable population of particles suitable for resembling a liquid mouthwash by swishing said powder delivery system, thereby generating fluid in the oral cavity without adding water.

Additionally, the present invention provides a method of achieving oral care benefits, comprising the steps of:
 a) providing a swishable powder delivery system having a content of at least two types of sugar alcohol particles with different particle size distributions and one or more active ingredients, the powder delivery system being a dry and flowable population of particles, optionally provided in an outer flowpack material,
 b) resembling a liquid mouthwash by swishing said powder delivery system, thereby generating fluid in the oral cavity without adding water.

Furthermore, the present invention provides a method of achieving oral care benefits, comprising the steps of:
 a) providing a swishable powder delivery system having a content of at least two types of sugar alcohol particles with different particle size distributions and one or more active ingredients, the powder delivery system being a dry and flowable population of particles, optionally provided in an outer flowpack material,
 b) subjecting the swishable powder delivery system into water, thereby obtaining an at least partly dissolved swishable powder delivery system, and
 c) swishing the at least partly dissolved swishable powder delivery system, thereby generating fluid in the oral cavity.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in connection with the word comprising or containing denote "one or more." The expression "one or more" is intended to mean one, two, three or more.

As used herein, the term "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

As used herein, the term "%" and "percent" refers to percent by weight, unless otherwise is stated.

In the present context, the phrase "population of particles" refers to a statistical population of particles. The population of particles may be characterized by a number of different parameters, e.g. statistical parameters such as distribution of particles, average particle size, particle size distribution width, etc. The population of particles may have subpopulations, such as DC sugar alcohol particles and non-DC sugar alcohol particles.

The term "particle size" relates to the ability of the particles to move through or be retained by sieve holes of a specific size. As used herein, the term "particle size" refers to the average particle size as determined according to European Pharmacopoeia 9.1 when using test method 2.9.38 particle size distribution estimation by analytical sieving, unless otherwise specifically is mentioned.

The term "particle" or similar wording is intended to denote a single, discrete composition of solid matter, such as a granule or individual elements in powder, having a certain size that may deviate considerable.

The powder system or powder delivery system provided in the present invention is generally provided as a powder where the individual particles are not further processed, such as in a direct compression process or compaction process. Hence, the powder system is not in form of a tablet or similar aggregation of powders. However, some degree of agglomeration of the particles of the present invention may occur either during storage of the powder system in the flow pack or to a minor degree during processing of the particles.

The term "flow pack" is intended to mean a wrapping containing the powder system according to the present invention, where the package is generally given the meaning in the field of flowpack technology. Generally, the powder system is applied during "flow" of the wrapping material in a machinery that allows an efficient process with high speed. Stick packs and sachets are examples of flow packs.

The term "powder system", "powder delivery system" or "formulation" is intended to be understood as the entire content of matter filled into the flowpack according to the invention, i.e. excluding the package or wrapping material surrounding the content. Hence, once reference is made to a "powder system", "powder delivery system" or a "formulation", then it includes the "population of particles" as a subsection as well as the one or more active ingredients but it may also include additional ingredients or particles.

As used herein, the term "dissolve" is the process where a particle enters a solvent (oral saliva) to yield a solution. Unless otherwise stated, dissolving implies a full dissolving of the compound in question. In some embodiments, the dissolution rate of the active ingredient is measured and shows an improvement compared to conventional powder formulations.

The term "in vivo release" or "in vivo testing of release" or similar wording intends to mean that the formulation is tested as outlined in the examples.

The term "in vitro release" or "in vitro testing of release" or similar wording intends to mean that the formulation is tested according to the examples, in particular according to General Monograph 2.9.25 in European Pharmacopoeia, 5th ed.

The term "release" in the present context is intended to mean under "in vitro" conditions if not stated otherwise. In particular, the "release rate" during a certain period of time is intended to mean the amount in percentage of active ingredient that is released during the period. In some embodiments, the process of releasing a substance corresponds to the substance being dissolved in saliva.

The term "sustained release" or "extended release" is herein intended to mean prolonged release over time. The term "rapid release" or "quick release" or "high release" is herein intended to mean a higher content released for a given period of time.

In the present context the term "turn into liquid" is intended to mean that the population of particles are either suspended or dissolved in saliva, perceived as liquid by a test person in accordance with the test procedure of induced saliva generation.

The term "delivery to the oral mucosa" or similar wording intends to mean that the formulation is tested according to the examples.

As used herein the term "nutraceutical ingredient", "biologically active ingredient" or simply "active ingredient" refers to a substance that is biologically active and has a physiological effect on the human body for the benefit of the human body or part thereof. Active ingredients include active pharmaceutical ingredients, but also other active substances, such as nutraceuticals, dietary supplements or oral care ingredients.

In the present context, the term "suitable for active pharmaceutical ingredients" refers to the formulation as a suitable vehicle for e.g. inclusion and delivery of active pharmaceutical ingredients. However, it is noted that the powder system may or may not include active pharmaceutical ingredients.

By the terms "water-insoluble gum base" or "gum base" or "gum base matrix" or similar wording is meant the mainly water-insoluble ingredients and hydrophobic gum base ingredients. The "gum base" may contain gum base polymers and plasticizers, waxes, emulsifiers, fats and/or fillers.

It should be noted that the terminology non-DC is easily understood within the field of technology. Suppliers of sugar alcohol provides clear guidance to the user as for the ability for use in relation to compression of tablets. A non-DC particle in this connection is referred to as a particle which is not expressly recommended by the supplier for compression. Examples of a non-DC grade of erythritol includes Zerose (TM) erythritol 16952F and Zerose erythritol 16961 supplied by Cargill. Further examples of non-DC sugar alcohol particles include non-DC xylitol as Xivia C from Dupont, non-DC isomalt as Isomalt GS from Beneo Paltinit, non-DC mannitol as C*Pharm Mannidex 16700 from Cargill, non DC maltitol as Maltisorb P200 from Roquette. Examples of a direct compressible (DC) grade of erythritol include Zerose™ DC 16966 also supplied by Cargill. Further examples of DC sugar alcohols include sorbitol particles provided as e.g. Neosorb® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab from Dupont.

Non-direct compressible (non-DC) sugar alcohols may include non-DC grades of Xylitol, non-DC grades of Erythritol, non-DC grades of Mannitol, non-DC grades of maltitol, non-DC grades of Lactitol, non-DC grades of Isomalt, or other suitable non-DC grades of sugar alcohols.

Direct compressible (DC) sugar alcohols may include sorbitol, which is DC by nature, DC grades of Xylitol, DC grades of Erythritol, DC grades of Mannitol, DC grades of maltitol, DC grades of Lactitol, DC grades of Isomalt or other suitable DC grades of sugar alcohols.

In an embodiment of the invention, the formulation comprises further ingredients selected from the group consisting of flavors, dry-binders, anti-caking agents, emulsifiers, antioxidants, enhancers, mucoadhesives, absorption enhancers, high intensity sweeteners, softeners, colors, active ingredients, water-soluble indigestible polysaccharides, water-insoluble polysaccharides or any combination thereof.

According to embodiments of the invention, the emulsifiers may be selected from the group consisting of sucrose ester of fatty acids (such as sucrose mono stearate), polyethylene glycol esters or ethers (PEG) (such as caprylocaproyl macrogol-8 glycerides and lauroyl macrogol-32-glycerides), mono- and diglyceride of fatty acids (such as glycerol monostearate, glycerol monolaurate, glyceryl behenate ester), acetic acid esters of mono- and diglycerides of fatty acids (Acetem), polyoxyethylene alkyl ethers, diacetyl tartaric ester of monoglycerides, lactylated monoglycerides, glycerophospholipids (such as lecithin), poloxamer (non-ionic block copolymer of ethylene oxide and propylene oxide), cyclodextrins, fatty acid esters of sorbitol (such as sorbitan monolaurate, sorbitan monostearate, sorbitan tristearate, polysorbates).

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, *eucalyptus*, and mint, fruit essence such as from apple, pear, peach, strawberry, apricot, raspberry, cherry, pineapple, and plum essence. The essential oils include peppermint, spearmint, menthol, *eucalyptus*, clove oil, bay oil, anise, thyme, cedar leaf oil, nutmeg, and oils of the fruits mentioned above.

Antioxidants suitable for use include butylated hydroxyanisole (BHA), butylated hydroxytoluene (BHT), betacarotenes, tocopherols, acidulants such as Vitamin C (ascorbic acid or corresponding salts (ascorbates)), propyl gallate, catechins, green tea extract other synthetic and natural types or mixtures thereof.

High intensity sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the high intensity sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another formulation component such as a resinous compound.

Usage level of the high-intensity sweetener will vary considerably and will depend on factors such as potency of the sweetener, rate of release, desired sweetness of the product, level and type of flavor used and cost considerations. Thus, the active level of high intensity sweetener may vary from about 0.001 to about 8% by weight (preferably from about 0.02 to about 8% by weight). When carriers used for encapsulation are included, the usage level of the encapsulated high-intensity sweetener will be proportionately higher.

The invention, if desired, may include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof. According to an embodiment of the invention, one preferred filler/texturizer is calcium carbonate.

In one embodiment the formulation according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramin, Diclofenac, Etoricoxib, Ibuprofen, Indometacin, Ketoprofen, Lumiracoxib, Morphine, Naproxen, Oxycodon, Parecoxib, Piroxicam, Pseudoefedrin, Rofecoxib, Tenoxicam, Tramadol, Valdecoxib, Calciumcarbonat, Magaldrate, Disulfiram, Bupropion, Nicotine, Azithromycin, Clarithromycin, Clotrimazole, Erythromycin, Tetracycline, Granisetron, Ondansetron, Prometazin, Tropisetron, Brompheniramine, Ceterizin, leco-Ceterizin, Chlorcyclizine, Chlorpheniramin, Chlorpheniramin, Difenhydramine, Doxylamine, Fenofenadin, Guaifenesin, Loratidin, des-Loratidin, Phenyltoloxamine, Promethazin, Pyridamine, Terfenadin, Troxerutin, Methyldopa, Methylphenidate, Benzalcon. Chloride, Benzeth. Chloride, Cetylpyrid. Chloride, Chlorhexidine, Ecabet-sodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc, Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonine, Phenobarbitol, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Caffeine, Ephedrine, Orlistat, Phenylephedrine, Phenylpropanolamin, Pseudoephedrine, Sibutramin, Ketoconazole, Nitroglycerin, Nystatin, Progesterone, Testosterone, Vitamin B12, Vitamin C, Vitamin A, Vitamin D, Vitamin E, green tea extract, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the powder. The active agents, for which a controlled and/or accelerated rate of release is desired, are primarily substances with a limited water-solubility, typically below 10 g/100 mL inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from ginkgo, the active components from propolis, the active components from *ginseng*, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, amino fluorides, stannous fluoride), phosphates, carbonates and selenium.

Cf furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Further examples of active agents are medicines of any type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocinelactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Further examples of active ingredients include dental products including Carbamide, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride.

Further examples of active ingredients include Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride Further examples of active ingredients include vitamins. Vitamins include A, B1, B2, B6, B12, Folinic acid, Folic acid, niacin, Pantothenic acid, biotine, C, D, E, K. Minerals include Calcium, phosphor, magnesium, iron, Zinc, Copper, Iod, Mangan, Crom, Selene, Molybden. Other active ingredients include: Q10®, enzymes. Natural drugs including *Ginkgo Biloba*, ginger, and fish oil.

Further examples of active ingredients include migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid. In a preferred embodiment the invention relates to the release of Nicotine and its salts.

In an advantageous embodiment of the invention the active ingredient is selected from active ingredients for the throat selected from acetylcysteine, ambroxol, amylmetacresol, benzocaine, bisacodyl, bismuth subsalicylate, bromhexine, cetirizine, cetylpyridinium, chlorhexidine, dextromethorphan hydrobromide, 2,4-dichlorobenzyl alcohol, doxylamine succinate, *eucalyptus* oil, flurbiprofen, glycerin, hexylresorcinol, lidocaine, menthol, myrrh, paracetamol, pectin, peppermint oil, phenol, phenylephrine, povidone-iodine, pseudoephedrine, ranitidine, simethicone, sodium docusate, spearmint, zinc, or any combination thereof active ingredients for the gastrointestinal tract selected from alginate, atenolol, aspirin (acetylsalicylic acid), ampicillin, aminosalicylates, anhydrous citric acid, aspirin, bisacodyl, bismuth subsalicylate, bupropion, caffeine, calcium, calcium carbonate, cetirizine, cimetidine, cisapride, clarithromycin, desloratadine, dexlansoprazole, diphenhydramine HCl, diphenhydramine citrate, dimenhydrinate, docusate erythromycin, dopamine, esomeprazole, famotidine, fexofenadine HCl, guaifenesin, hydrotalcite, ibuprofen, ketoprofen, lactase enzyme, lansoprazole, loratadine, lorcaserin, loperamide, loperamide HCl, magnesium, magnesium carbonate, magnesium hydroxide, melatonin, methamphetamine HCl, metoclopramide, metronidazole, montelukast, mycostatin, naltrexone, naproxen, naproxen sodium, nizatidine, omeprazole, ondansetron, orlistat, pantoprazole, paracetamol (acetaminophen), pectin, phentermine HCl, polypodium leucotomos, prednisolone, prednisone, progesterone, propranolol, propantheline bromide, pseudoephedrine HCl, phentermine, rabeprazole, ranitidine, roflumilast, scopoloamine butyl hydroxide, simethicone, sodium, sodium bicarbonate, sodium docusate, sumatriptan, testosterone, tetracycline, topiramate, vitamin A, vitamin B, vitamin B12, vitamin C (ascorbic acid), vitamin D, and vitamin E, vitamin K, or any combination thereof, and active ingredients for buccal absorption selected from atenolol, baclofen, caffeine, carvedilol, chlorpheniramine, chlorpheniramine maleate, fluticasone propionate, maleate, desmopressin, diltiazem hydrochloride, doxylamine succinate, mycostatin, nicotine, nifedipine, nitroglycerin, omeprazole, ondansetron, oxymetazoline HCl, oxytocin, phenylephrine, piroxicam, prednisone, propranolol, salbutamol sulphate, scopoloamine butyl hydroxide, sumatriptan, triamcinolonacetonid, and any combination thereof.

The active ingredient may also be one or more cannabinoids selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). More preferably the one or more cannabinoid is CBD or THC.

In an embodiment of the invention, the formulation comprises particles comprising gum base, and wherein the formulation is designed to be masticated into a coherent residual containing water-insoluble components.

The application of gum may in the present context may invoke a delay of release for active ingredients and this may again promote the buccal and upper throat absorption of active pharmaceutical ingredient when this is released from the formulation during mastication.

In an embodiment of the invention, the formulation contains particles comprising gum base, and wherein the gum base comprises at least 5% by weight of elastomer.

When including gum base in the formulation sugar alcohols typically constitute from about 5 to about 95% by weight, more typically about 20 to about 80% by weight such as 30 to 70% or 30 to 60% by weight of the formulation.

In such an embodiment of the invention, the formulation further comprises, beside the already described sugar alcohols, materials selected from the group consisting of bulk sweeteners, flavors, dry-binders, anti-caking agents, emulsifiers, antioxidants, enhancers, absorption enhancers, buffers, high intensity sweeteners, softeners, colors, or any combination thereof.

EXAMPLES

Example 1

Procedure for Particle Size Fractioning

Different sugar alcohols were fractionized according to particle size by performing analyses of the particle size distribution of the various raw materials. The analyses were performed on a Retsch AS 200 control sieve shaker with a stack of 4-5 sieves. The mesh sizes were selected based on the raw material. The procedure for the fractioning was as follows: The sieves were stacked on the shaker with the largest mesh size on top and descending sizes downwards. Two small balls were added to each sieves with a mesh size of 250 µm or less to increase the distribution of fine particles on the sieve. A sample of 100 g sugar alcohol was placed on top of the sieve stack, the lid was fastened, and the shaker was started. The sample was shaken for 15 min with an amplitude of 1.5 mm. Upon completion of analysis, the content of each sieve was determined giving the particle size distribution of the raw material.

Example 2

Xylitol Sugar Alcohol Particles

Xylitol in different grades was provided and was fractionized according to Example 1. Table 1 below indicates the various xylitol particles applied.

Granulated directly compressible (DC) xylitol was provided by DuPont under the trade name Xylitab® 200. The product is a commercially available product that has been granulated in a wet-granulation process with 2% sodium carboxymethylcellulose as binder.

Crystalline non-directly compressible (non-DC) xylitol was provided by DuPont under the trade name Xivia C. This xylitol grade was milled to provide a milled crystalline xylitol grade.

TABLE 1

Flow properties of different xylitol grades provided and fractions hereof.

| No. | Grade | Particle size | Flow properties (Good/Acceptable(Acc)/Poor) |
|---|---|---|---|
| | | Xylitol Granulated | |
| 1 | Xylitab ® 200 | X > 800 µm Max 5% X < 150 µm Max 12% X < 71 µm Max 5% | Good |
| 2 | Xylitab ® 200 | 400 µm < X < 500 µm | Good |
| 3 | Xylitab ® 200 | 250 µm < X < 400 µm | Good |
| 4 | Xylitab ® 200 | 90 µm < X < 250 µm | Good |
| | | Non-granulated | |
| 5 | Xivia C | X < 50 µm Max. 5% X < 1400 µm Min. 98% | Good |
| 6 | Xivia C | 500 µm < X < 1000 µm | Good |
| 7 | Xivia C | 90 µm < X < 250 µm | Acc. |
| 8 | Milled xylitol | X > 200 µm Max. 15% X > 40 µm Min. 50% | Poor |
| 9 | Milled xylitol | 250 µm < X < 400 µm | Good |
| 10 | Milled xylitol | <90 µm | Poor |

Example 3

Maltitol Sugar Alcohol Particles

Maltitol with different particle size distributions was provided. Table 2 below indicates the various maltitol particles applied.

Granulated DC maltitol was provided by Roquette under the trade name SweetPearl® P300 DC. The product is a commercially available product.

Crystalline non-DC maltitol was provided by Roquette under the trade name SweetPearl® P200. The product is a commercially available product.

TABLE 2

Flow properties of different maltitol grades provided.

| No. | Grade | Particle size | Flow properties (Good/Acceptable(Acc)/Poor) |
|---|---|---|---|
| | | Maltitol Granulated | |
| 11 | SweetPearl ® P300 DC | X > 500 µm Max. 5% X > 100 µm Min. 80% | Good |
| | | Non-granulated | |
| 12 | SweetPearl ® P200 | X > 500 µm Max. 5% X > 100 µm Min. 40% | Acc. |

Example 4

Isomalt Sugar Alcohol Particles

Isomalt in different grades was provided and was fractionized according to Example 1. Table 3 below indicates the various isomalt particles applied.

Granulated DC isomalt was provided by Beneo Palatinit under the trade name Isomalt DC 101. The product is a commercially available product.

Crystalline non-DC isomalt was provided by Beneo Palatinit under the trade name Isomalt GS. The product is a commercially available product.

Granulated DC isomalt was provided by Beneo Palatinit under the trade name galenIQ™ 720. The product is a commercially available product.

TABLE 3

Flow properties of different isomalt grades provided and fractions hereof.

| No. | Grade | Particle size | Flow properties (Good/Acceptable(Acc)/Poor) |
|---|---|---|---|
| | | Isomalt Granulated | |
| 13 | Isomalt DC 101 | 100 μm < X < 800 μm Min 90% | Good |
| 14 | Isomalt DC 101 | X > 500 μm | Good |
| 15 | Isomalt DC 101 | 90 μm < X < 250 μm | Good |
| 16 | Isomalt DC 101 | X < 90 μm | Poor |
| 17 | galenIQ ™ 720 | X > 500 μm Max. 5% X > 250 μm 20-70% X < 63 μm Max. 15% | Good |
| 18 | galenIQ ™ 720 | 250 μm < X < 500 μm | Good |
| 19 | galenIQ ™ 720 | 90 μm < X < 250 μm | Good |
| 20 | galenIQ ™ 720 | X < 90 μm | Poor |
| | | Non-granulated | |
| 21 | Isomalt GS | <1500 μm | Good |
| 22 | Isomalt GS | 500 μm < X < 1000 μm | Good |
| 23 | Isomalt GS | 250 μm < X < 500 μm | Good |
| 24 | Isomalt GS | 90 μm < X < 250 μm | Good |

Example 5

Erythritol Sugar Alcohol Particles

Erythritol with different particle size distributions was provided and further combined with one or more additional sugar alcohol particles according to the invention. Table 4 below indicates the various erythritol particles applied.

Non-DC erythritol particles were provided by Cargill under the trade name Zerose™ 16952. The product is a commercially available product that has been processed by fermentation of carbohydrates. This grade was further fractionized according to Example 1.

Non-DC erythritol particles were provided by Jungbunzlauer under the trade name ERYLITE®. The product is a commercially available product that has been processed by fermentation of carbohydrates.

Non-DC erythritol particles were provided by Cargill under the trade name Zerose™ 16961. The product is a commercially available product that has been processed by fermentation of carbohydrates.

TABLE 4

Flow properties of different erythritol grades provided and fractions hereof.

Erythritol

| No. | Grade | Particle size | Flow properties (Good/Acceptable(Acc)/Poor) |
|---|---|---|---|
| 25 | Zerose ™ 16952 | X < 250 μm max 20% | Good |
| 26 | Zerose ™ 16952 | 500 μm < X < 1000 μm | Good |
| 27 | Zerose ™ 16952 | 90 μm < X < 250 μm | Good |
| 28 | ERYLITE ® | X > 800 μm max. 15% X < 300 μm max. 10% | Good |
| 29 | Zerose ™ 16961 | X > 150 μm max 5% X > 250 μm max 0.5% | Poor |

Example 6

Mannitol Sugar Alcohol Particles

Mannitol was provided and further combined with one or more additional sugar alcohol particles according to the invention. Table 5 below indicates the various mannitol particles applied.

Non-DC mannitol particles were provided by Cargill under the trade name C*Pharm Mannidex 16700. The product is a commercially available product. This grade was further fractionized according to Example 1.

TABLE 5

Flow properties of the mannitol grade provided and fractions hereof.

| No. | Grade | Particle size | Flow properties (Good/Acceptable(Acc)/Poor) |
|---|---|---|---|
| | | Mannitol Non-granulated | |
| 30 | C*Pharm Mannidex 16700 | X < 355 μm Min. 95% X > 180 μm Max. 40% | Poor |
| 31 | C*Pharm Mannidex 16700 | 90 μm < X < 250 μm | Acc. |
| 32 | C*Pharm Mannidex 16700 | <90 μm | Poor |

Example 7

Sorbitol Sugar Alcohol Particles

Sorbitol with different particle size distributions was provided and further combined with one or more additional sugar alcohol particles according to the invention. Table 6 below indicates the various sorbitol particles applied.

Sorbitol sugar alcohol particles were provided by PharmSorbidex from Cargill under the trade name C*PharmSorbidex P 16656. The product is a commercially available product that has been processed by hydrogenation of sugars. This grade was further fractionized according to Example 1.

Sorbitol sugar alcohol particles were provided by Cargill under the trade name C*Sorbidex™ S 16607. The product is a commercially available product that has been processed by hydrogenation of sugars.

TABLE 6

Flow properties of different sorbitol grades provided and fractions hereof. Sorbitol

| No. | Grade | Particle size | Flow properties (Good/Acceptable(Acc)/Poor) |
|---|---|---|---|
| 35 | C*PharmSorbidex P 16656 | X > 250 μm 20-45%<br>X > 500 μm Max. 0.5%<br>X < 63 μm Max. 7.5% | Good |
| 36 | C*PharmSorbidex P 16656 | 250 μm < X < 500 μm | Good |
| 37 | C*PharmSorbidex P 16656 | <90 μm | Acc. |
| 38 | C*Sorbidex ™ S 16607 | X < 100 μm 17-30%<br>X > 300 μm Max. 3%<br>X < 40 μm 3.5-11% | Good |

Example 8

Packaging for Powder Delivery System

The appropriate amount of powder delivery system was measured (between 0.5-2 g) and loaded into a 1.0 inch×2.5 inch foil bag with a tear notch. The foil bag was sealed using heat-sealing providing the individual portioned-packed powder delivery system.

Example 9

Combination of Two Sugar Alcohol Particles

Various types of two sugar alcohol particles from Examples 2-7 were mixed in a 1:1 weight ratio. The two types of sugar alcohol particles were mixed according to the following procedure: An exact and equal amount of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Examples 2-4 were combined with non-directly compressible sugar alcohol particles from Examples 5-6.

TABLE 7

Different combinations of granulated sugar alcohol particles and non-DC sugar alcohol particles.

| | | Combination of two samples | |
|---|---|---|---|
| No. | Examples | Sample no. | Sample no. |
| 91 | 2 + 5 | 1 | 29 |
| 92 | 2 + 5 | 3 | 27 |
| 93 | 3 + 6 | 11 | 31 |
| 94 | 3 + 6 | 11 | 30 |
| 95 | 4 + 5 | 13 | 29 |
| 96 | 2 + 6 | 1 | 30 |

Example 9A

Combination of Two Sugar Alcohol Particles

Various types of two sugar alcohol particles from Examples 2-7 were mixed in different weight ratio. The two types of sugar alcohol particles were mixed according to the following procedure: An exact amount of each type of sugar alcohol particles was measured by weight (between 3-5 g of each). The two types of sugar alcohol particles were combined in a 70×100 mm plastic bag at ambient conditions and the content in the bag was mixed thoroughly. The weight ratios between granulated sugar alcohol particles from Examples 2-4 and non-directly compressible sugar alcohol particles from Examples 5-6 were respectively 0.1, 0.2, 0.5, 1, 3, 5 and 6.

Example 9B

Combination of Two Sugar Alcohol Particles

Various types of two sugar alcohol particles from Examples 2-7 were mixed in a 1:1 weight ratio. The two types of sugar alcohol particles were mixed according to the following procedure: An exact and equal amount of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Examples 2-4 were combined with non-directly compressible sugar alcohol particles from Examples 5-6.

TABLE 7A

Different combinations of granulated sugar alcohol particles and non-DC sugar alcohol particles.

| | | Combination of two samples | |
|---|---|---|---|
| No. | Examples | Sample no. | Sample no. |
| 97A | 2 + 5 | 1 | 27 |
| 97B | 3 + 5 | 11 | 27 |
| 97C | 3 + 5 | 11 | 29 |
| 97D | 4 + 5 | 13 | 27 |
| 97E | 4 + 6 | 13 | 30 |

Example 9C

Combination of Two Sugar Alcohol Particles with Non-DC Particles

Various types of two sugar alcohol particles from Examples 2-7 were mixed in a 1:1 weight ratio. The two types of sugar alcohol particles were mixed according to the following procedure: An exact and equal amount of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Examples 2-4 were combined with non-directly compressible sugar alcohol particles from Examples 5-6.

TABLE 7B

Different combinations of granulated xylitol and non-DC sugar alcohol particles with a small particle size.

| | | Combination of two samples | |
|---|---|---|---|
| No. | Examples | Sample no. | Sample no. |
| 98A | 2 + 5 | 1 | 27 |
| 98B | 2 + 5 | 1 | 29 |
| 98C | 2 + 5 | 1 | 25* |
| 98D | 2 + 5 | 1 | 28** |

*comparative example with more than 80% of the particles above 250 microns, and
**comparative example with less than 10% of the particles below 300 microns.

Example 9D

Combination of Two Sugar Alcohol Particles with Non-DC Particles in Varying Amounts Various types of two sugar alcohol particles from Examples 2 and 5 were mixed in a varying weight ratio. The two types of sugar alcohol particles were mixed according to the following procedure: Varying amounts of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Examples 2 were combined with non-directly compressible sugar alcohol particles from Examples 5.

TABLE 7C

Different combinations of granulated xylitol and non-DC sugar alcohol particles with a small particle size.

| | | Combination of two samples | |
|---|---|---|---|
| No. | Examples | Sample no. | Sample no. |
| 99A | 2 + 5 | 1 (33%) | 27 (67%) |
| 99B | 2 + 5 | 1 (33%) | 29 (67%) |
| 99C | 2 + 5 | 1 (67%) | 27 (33%) |
| 99D | 2 + 5 | 1 (67%) | 29 (33%) |
| 99E | 2 + 5 | 1 (33%) | 25* (67%) |
| 99F | 2 + 5 | 1 (67%) | 25* (33%) |
| 99G | 2 + 5 | 1 (33%) | 28** (67%) |
| 99H | 2 + 5 | 1 (67%) | 28** (33%) |

*comparative example with more than 80% of the particles above 250 microns, and
**comparative example with less than 10% of the particles below 300 microns. Percentage in weight percentage.

Example 9E

Combination of Two Sugar Alcohol Particles with Non-DC Particles in Varying Total Oral Portions Various types of two sugar alcohol particles from Examples 2 and 5 were mixed in a 1:1 weight ratio. The two types of sugar alcohol particles were mixed according to the following procedure: The amounts of each type of sugar alcohol particles was measured by weight (1, 2, 3 and 5 g of each). The two types of sugar alcohol particles were combined in a 70×100 mm plastic bag at ambient conditions and the content in the bag was mixed thoroughly. In this example granulated sugar alcohol particles from Examples 2 were combined with non-directly compressible sugar alcohol particles from Examples 5.

TABLE 7D

Different combinations of granulated xylitol and non-DC sugar alcohol particles with a small particle size.

| | | Combination of two samples | |
|---|---|---|---|
| No. | Examples | Sample no. | Sample no. |
| 100A | 2 + 5 (1 g total) | 1 | 29 |
| 100B | 2 + 5 (2 g total) | 1 | 29 |
| 100C | 2 + 5 (3 g total) | 1 | 29 |
| 100D | 2 + 5 (4 g total) | 1 | 29 |
| 100E | 2 + 5 (1 g total) | 1 | 25* |
| 100F | 2 + 5 (2 g total) | 1 | 25* |
| 100G | 2 + 5 (3 g total) | 1 | 25* |
| 100H | 2 + 5 (5 g total) | 1 | 25* |

*comparative example with more than 80% of the particles above 250 microns. Percentage in weight percentage.

Example 10

Combination of Two Sugar Alcohol Particles

Various types of two sugar alcohol particles from Examples 2-7 were mixed in a 1:1 weight ratio. The two types of sugar alcohol particles were mixed according to the following procedure: An exact and equal amount of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Examples 2-4 were combined with sorbitol sugar alcohol particles from Example 7.

TABLE 8

Different combinations of sugar alcohol particles with sorbitol sugar alcohol particles.

| | | Combination of two samples | |
|---|---|---|---|
| No. | Examples | Sample no. | Sample no. |
| 101 | 2 + 7 | 1 | 38 |
| 102 | 3 + 7 | 11 | 38 |
| 103 | 4 + 7 | 13 | 35 |
| 104 | 2 + 7 | 3 | 38 |
| 105 | 3 + 7 | 11 | 35 |

Example 10A

Combination of Two Sugar Alcohol Particles

Various types of two sugar alcohol particles from Examples 2-7 were mixed in different weight ratio. The two types of sugar alcohol particles were mixed according to the following procedure: An exact amount of each type of sugar alcohol particles was measured by weight (between 3-5 g of each). The two types of sugar alcohol particles were combined in a 70×100 mm plastic bag at ambient conditions and the content in the bag was mixed thoroughly. The weight ratios between granulated sugar alcohol particles from Examples 2-4 and sorbitol sugar alcohol particles from Example 7 were respectively 0.1, 0.2, 0.5, 1, 3, 5 and 6.

Example 10B

Combination of Two Sugar Alcohol Particles

Various types of two sugar alcohol particles from Examples 2-7 were mixed in a 1:1 weight ratio. The two types of sugar alcohol particles were mixed according to the following procedure: An exact and equal amount of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Examples 2-4 were combined with sorbitol sugar alcohol particles from Example 7.

TABLE 8A

Different combinations of sugar alcohol particles with sorbitol sugar alcohol particles.

| No. | Examples | Combination of two samples Sample no. | Sample no. |
|---|---|---|---|
| 106A | 2 + 7 | 1 | 35 |
| 106B | 2 + 7 | 1 | 37 |
| 106C | 3 + 7 | 11 | 35 |
| 106D | 3 + 7 | 11 | 38 |
| 106E | 4 + 7 | 13 | 37 |
| 106F | 4 + 7 | 13 | 38 |

Example 10C

Combination of Two Sugar Alcohol Particles with DC Particles that are not Granulated Sugar Alcohol Particles Various types of two sugar alcohol particles from Examples 2 and 7 were mixed in a 1:1 weight ratio. The two types of sugar alcohol particles were mixed according to the following procedure: An exact and equal amount of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Example 2 were combined with sorbitol sugar alcohol particles from Example 7.

TABLE 8B

Different combinations of sugar alcohol particles with sorbitol sugar alcohol particles.

| No. | Examples | Combination of two samples Sample no. | Sample no. |
|---|---|---|---|
| 107A | 2 + 7 | 1 | 35 |
| 107B | 2 + 7 | 1 | 37 |
| 107C | 2 + 7 | 1 | 38 |
| 107D | 2 + 7 | 1 | 36* |

*comparative example with a particle size of between 250 and 500 microns.

Example 10D

Combination of Two Sugar Alcohol Particles with DC Particles that are not Granulated Sugar Alcohol Particles Various types of two sugar alcohol particles from Examples 2 and 7 were mixed in a varying weight ratio. The two types of sugar alcohol particles were mixed according to the following procedure: Varying amounts of each type of sugar alcohol particles was measured by weight (between 3-5 g of each). The two types of sugar alcohol particles were combined in a 70×100 mm plastic bag at ambient conditions and the content in the bag was mixed thoroughly. In this example granulated sugar alcohol particles from Example 2 were combined with sorbitol sugar alcohol particles from Example 7.

TABLE 8C

Different combinations of sugar alcohol particles with sorbitol sugar alcohol particles.

| No. | Examples | Combination of two samples Sample no. | Sample no. |
|---|---|---|---|
| 108A | 2 + 7 | 1 (33%) | 35 (67%) |
| 108B | 2 + 7 | 1 (67%) | 35 (33%) |
| 108C | 2 + 7 | 1 (33%) | 37 (67%) |
| 108D | 2 + 7 | 1 (67%) | 37 (33%) |
| 108E | 2 + 7 | 1 (33%) | 38 (67%) |
| 108F | 2 + 7 | 1 (67%) | 38 (33%) |
| 108G | 2 + 7 | 1 (33%) | 36* (67%) |
| 108H | 2 + 7 | 1 (67%) | 36* (33%) |

*comparative example with a particle size of between 250 and 500 microns. Percentage in weight percentage.

Example 10E

Combination of Two Sugar Alcohol Particles with DC Particles that are not Granulated Sugar Alcohol Particles in Varying Total Oral Portions Various types of two sugar alcohol particles from Examples 2 and 7 were mixed in a 1:1 weight ratio. The two types of sugar alcohol particles were mixed according to the following procedure: The amounts of each type of sugar alcohol particles was measured by weight (1, 2, 3 and 5 g of each). The two types of sugar alcohol particles were combined in a 70×100 mm plastic bag at ambient conditions and the content in the bag was mixed thoroughly. In this example granulated sugar alcohol particles from Example 2 were combined with sorbitol sugar alcohol particles from Example 7.

TABLE 8D

Different combinations of sugar alcohol particles with sorbitol sugar alcohol particles.

| No. | Examples | Combination of two samples Sample no. | Sample no. |
|---|---|---|---|
| 109A | 2 + 7 (1 g total) | 1 | 35 |
| 109B | 2 + 7 (2 g total) | 1 | 35 |
| 109C | 2 + 7 (3 g total) | 1 | 35 |
| 109D | 2 + 7 (5 g total) | 1 | 35 |
| 109E | 2 + 7 (1 g total) | 1 | 36* |
| 109F | 2 + 7 (2 g total) | 1 | 36* |
| 109G | 2 + 7 (3 g total) | 1 | 36* |
| 109H | 2 + 7 (5 g total) | 1 | 36* |

*comparative example with a particle size of between 250 and 500 microns. Percentage in weight percentage.

Example 11

Combination of Three Sugar Alcohol Particles

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 3-5 g of each). The three types of sugar alcohol particles were combined in a 70×100 mm plastic bag at ambient conditions and the content in the bag was mixed thoroughly.

TABLE 9

Different combinations of sugar alcohol particles.

| | | Combination of three samples | | |
|---|---|---|---|---|
| No. | Examples | Sample no. | Sample no. | Sample no. |
| 111 | 2 + 5 + 7 | 1 | 29 | 35 |
| 112 | 2 + 5 + 7 | 1 | 29 | 38 |
| 113 | 3 + 5 + 7 | 11 | 29 | 38 |
| 114 | 2 + 4 + 7 | 1 | 17 | 35 |
| 115 | 2 + 5 + 6 | 1 | 28 | 30 |
| 116 | 2 + 4 + 7 | 8 | 17 | 35 |
| 117 | 2 + 5 + 6 | 1 | 29 | 30 |
| 118 | 3 + 5 + 7 | 11 | 29 | 35 |
| 119 | 4 + 5 + 7 | 17 | 29 | 38 |
| 120 | 4 + 2 + 7 | 17 | 8 | 38 |

Example 11A

Combination of Three Sugar Alcohol Particles

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 3-5 g of each). The three types of sugar alcohol particles were combined in a 70×100 mm plastic bag at ambient conditions and the content in the bag was mixed thoroughly.

TABLE 9B

Different combinations of sugar alcohol particles.

| | | Combination of three samples | | |
|---|---|---|---|---|
| No. | Examples | Sample no. | Sample no. | Sample no. |
| 107A | 2 + 5 + 6 | 1 | 28 | 30 |
| 107B | 2 + 5 + 6 | 1 | 29 | 30 |
| 107C | 2 + 4 + 7 | 1 | 17 | 37 |
| 107D | 2 + 4 + 7 | 1 | 17 | 38 |
| 107E | 2 + 5 + 7 | 1 | 29 | 35 |
| 107F | 2 + 5 + 7 | 1 | 29 | 37 |
| 107G | 2 + 5 + 7 | 1 | 27 | 35 |
| 107H | 2 + 5 + 7 | 1 | 27 | 37 |
| 107I | 2 + 5 + 7 | 1 | 27 | 38 |
| 107J | 3 + 5 + 7 | 11 | 29 | 37 |
| 107K | 3 + 5 + 7 | 11 | 27 | 37 |
| 107L | 3 + 5 + 7 | 11 | 27 | 38 |
| 107M | 4 + 5 + 7 | 13 | 29 | 37 |
| 107N | 4 + 5 + 7 | 13 | 29 | 38 |
| 107O | 4 + 5 + 7 | 13 | 27 | 37 |
| 107P | 4 + 5 + 7 | 13 | 27 | 38 |
| 107Q | 4 + 6 + 7 | 13 | 30 | 37 |
| 107R | 2 + 6 + 7 | 1 | 30 | 37 |
| 107S | 3 + 6 + 7 | 11 | 30 | 37 |
| 107T | 2 + 4 + 7 | 8 | 17 | 37 |
| 107U | 2 + 4 + 7 | 8 | 17 | 38 |

Example 11B

Combination of Three Sugar Alcohol Particles

Various types of two sugar alcohol particles from Examples 2-7 were mixed in different weight ratio. The three types of sugar alcohol particles were mixed according to the following procedure: An exact amount of each type of sugar alcohol particles was measured by weight (between 3-5 g of each). The three types of sugar alcohol particles were combined in a 70×100 mm plastic bag at ambient conditions and the content in the bag was mixed thoroughly.

Example 11C

Combination of Three Sugar Alcohol Particles with Flow Promoting Agents

The samples from Example 11 were tested with different flow promoting agents. All samples were tested with a) silicium dioxide in an amount of 1% by weight of the sample and b) silicium dioxide in an amount of 2% by weight of the sample. Also, all samples were tested with c) rice hulls provided by Ribus under the brand name Nu-Flow in an amount of 2% by weight of the sample. These rice hulls have a particles size of below 74 microns.

Example 12

Combination of Three Sugar Alcohol Particles with Further Additives

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 3-5 g of each). The three types of sugar alcohol particles were combined in a 70×100 mm plastic bag at ambient conditions and the content in the bag was mixed thoroughly. Further additives were included in order to enhance the sweetness profile and obtain different flavor directions. The powder delivery system were included in a flow-pack according to Example 8.

TABLE 10

Different combinations of sugar alcohol particles including high-intensity sweeteners and flavors.

| | | Formulation with additional ingredients (% by weight) | |
|---|---|---|---|
| No. | Sample no. | HIS | Flavor |
| 121 | 111 | Sucralose (0.2%) | Mint (2.0%) |
| 122 | 112 | Sucralose (0.2%) | Mint (2.0%) |
| 123 | 113 | Sucralose (0.2%) | Mint (2.0%) |
| 124 | 114 | Sucralose (0.2%) | Mint (2.0%) |
| 125 | 115 | Sucralose (0.2%) | Mint (2.0%) |
| 126 | 112 | Stevia (0.1%) | Raspberry (1.0%) |
| 127 | 112 | Stevia (0.1%) | Eucalyptus (1.0%) |
| 128 | 112 | Acesulfame K (0.1%) | Orange (1.0%) |
| 129 | 112 | Acesulfame K (0.1%) | Coffee (0.5%) |

Example 13

Combination of Three Sugar Alcohol Particles with Effervescence Ingredients

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 3-5 g of each). The three types of sugar alcohol particles were combined in a 70×100 mm plastic bag at ambient conditions and the content in the bag was mixed thoroughly. Further effervescence ingredients were included in order to generate a fizzy sensation in the mouth. In addition, to some of the samples other active ingredients were added. The powder delivery system were included in a flow-pack according to Example 8.

TABLE 11

Different combinations of sugar alcohol particles and further components.

Formulation with effervescence ingredients (% by weight)

| No. | Sample no. | NaHCO3 | Citric acid | Active ingredient |
|---|---|---|---|---|
| 131 | 111 | 1.5% | 3% | — |
| 132 | 112 | 1.5% | 3% | — |
| 133 | 113 | 1.5% | 3% | — |
| 134 | 114 | 1.5% | 3% | — |
| 135 | 115 | 1.5% | 3% | — |
| 136 | 112 | 1.5% | 3% | Sodium ascorbate (16.7%) |
| 137 | 112 | 1.5% | 3% | Zink gluconate (3.5%) |

Example 14

Combination of Three Sugar Alcohol Particles with Immune Active Ingredients

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 3-5 g of each). The three types of sugar alcohol particles were combined in a 70×100 mm plastic bag at ambient conditions and the content in the bag was mixed thoroughly. Further immune active ingredients were included in order to attain an immune enhancing effect. The powder delivery system were included in a flow-pack according to Example 8.

TABLE 12

Different combinations of sugar alcohol particles and active ingredients.

Formulation with immune active ingredients (% by weight)

| No. | Sample no. | Active ingredient 1 | Active ingredient 2 | Active ingredient 3 |
|---|---|---|---|---|
| 141 | 112 | Elderberry extract (15.0%) | — | — |
| 142 | 112 | Sodium ascorbate (25.0%) | Zink gluconate (3.5%) | — |
| 143 | 112 | Echinacea (3.0%) | Sodium ascorbate (3.4%) | Zink gluconate (4.5%) |
| 144 | 112 | Rose hip (17.4%) | Sodium ascorbate (10.5%) | Ascorbic acid (3.1%) |
| 145 | 113 | Elderberry extract (15.0%) | — | — |
| 146 | 113 | Sodium ascorbate (25.0%) | Zink gluconate (0.5%) | — |
| 147 | 113 | Echinacea (15.0%) | Sodium ascorbate (25.0%) | Zink gluconate (0.5%) |
| 148 | 113 | Rose hip (17.4%) | Sodium ascorbate (10.5%) | Ascorbic acid (3.1%) |
| 148A | 112 | Sodium ascorbate (25.0%) | Zink citrate (2.0%) | — |
| 148B | 112 | Echinacea (3.0%) | Sodium ascorbate (10.0%) | Zink citrate (2.0%) |
| 148C | 113 | Sodium ascorbate (25.0%) | Zink citrate (2.0%) | — |
| 148D | 113 | Echinacea (3.0%) | Sodium ascorbate (10.0%) | Zink citrate (2.0%) |

Example 15

Combination of Three Sugar Alcohol Particles with Oral Care Active Ingredients

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 1-3 g of each). The three types of sugar alcohol particles were combined in a 70×100 mm plastic bag at ambient conditions and the content in the bag was mixed thoroughly. Further oral care active ingredients were included in order to attain oral benefits like caries protection, remineralization, and plaque removal. The powder delivery system were included in a flow-pack according to Example 8.

TABLE 13

Different combinations of sugar alcohol particles and active ingredients.

Formulation with oral care active ingredients (% by weight)

| No. | Sample no. | Active ingredient 1 | Active ingredient 2 | Active ingredient 3 |
|---|---|---|---|---|
| 151 | 112 | Sodium fluoride (0.03%) | Zinc acetate (0.6%) | — |
| 152 | 112 | Calcium carbonate (4.7%) | Sodium pyrophosphate (0.34%) | — |
| 153 | 112 | Sodium fluoride (0.04%) | Sodium bicarbonate (0.38%) | Zinc acetate (0.6%) |
| 154 | 112 | Calcium pyrophosphate (6.8%) | Sodium bicarbonate (0.38%) | Sodium fluoride (0.03%) |
| 155 | 113 | Sodium fluoride (0.03%) | Zinc acetate (0.6%) | — |
| 156 | 113 | Calcium carbonate (4.7%) | Sodium pyrophosphate (0.34%) | — |
| 157 | 113 | Sodium fluoride (0.04%) | Sodium bicarbonate (0.38%) | Zinc acetate (0.6%) |
| 158 | 113 | Calcium pyrophosphate (6.8%) | Sodium bicarbonate (0.38%) | Sodium fluoride (0.03%) |
| 158A | 112 | Essential oils* (0.4%) | — | — |
| 158B | 112 | Essential oils* (0.4%) | — | Zinc acetate (1.0%) |
| 158C | 113 | CPC** (0.04%) | — | — |
| 158D | 113 | CPC** (0.04%) | — | Zinc acetate (1.0%) |

*Amount denotes essential oils total in their pure form and include menthol, methyl salicylate, cineole and thymol.
**CPC include cetyl pyridinium chloride.

Example 16

Combination of Three Sugar Alcohol Particles with Energy Active Ingredients

Various types of three sugar alcohol particles from Examples 2-7 were mixed in a 1:1:1 weight ratio. The three types of sugar alcohol particles were mixed according to the following procedure: An exact and equal amount of each type of sugar alcohol particles was measured by weight (between 3-5 g of each). The three types of sugar alcohol particles were combined in a 70×100 mm plastic bag at ambient conditions and the content in the bag was mixed thoroughly. Furthermore, caffeine and a pre-blend of the B-vitamins: B6, niacin and B12 were included in order to obtain an energizing effect. In addition, flavor and HIS were added to enhance the sweetness profile and obtain different flavor directions. The powder delivery system were included in a flow-pack according to Example 8.

TABLE 14

Different combinations of sugar alcohol particles and active ingredients.

Formulation with energy active ingredients (% by weight)

| No. | Sample no. | Caffeine | Preblend of B-vitamins |
|-----|------------|----------|------------------------|
| 161 | 111 | 5.0% | — |
| 162 | 112 | 5.0% | 1.35% |
| 163 | 113 | 5.0% | 1.35% |
| 164 | 114 | 5.0% | — |
| 165 | 115 | 5.0% | — |

Example 16A

Combination of Three Sugar Alcohol Particles with Different Active Ingredients

Various types of three sugar alcohol particles from Examples 2-7 were mixed in a 1:1:1 weight ratio. The three types of sugar alcohol particles were mixed according to the following procedure: An exact and equal amount of 500 mg of each type of sugar alcohol particles was measured by weight for a total weight of 1500 mg. The three types of sugar alcohol particles were combined in a 70×100 mm plastic bag at ambient conditions and the content in the bag was mixed thoroughly. The powder delivery system were included in a flow-pack according to Example 8.

TABLE 14A

Different combinations of sugar alcohol particles and active ingredients.

Formulation with active ingredients (total of 1500 mg sugar alcohol particles + varying amounts of active ingredients)

| No. | Sample no. | Active ingredient 1 | Active ingredient 2 | Active ingredient 3 |
|-----|------------|---------------------|---------------------|---------------------|
| 165A | 112 | acetaminophen (325 mg) | phenylephrine (5 mg) | Dextromethorphan (10 mg) |
| 165B | 113 | acetaminophen (500 mg) | phenylephrine (5 mg) | Dextromethorphan (10 mg) |
| 165C | 112 | acetaminophen (325 mg) | phenylephrine (5 mg) | Dextromethorphan (10 mg) + guaifenesin (100 mg) |
| 165D | 112 | acetaminophen (325 mg) | phenylephrine (5 mg) | Dextromethorphan (10 mg) + guaifenesin (200 mg) |
| 165E | 112 | Diphenhydramine (25 mg) | — | — |
| 165F | 113 | Diphenhydramine (25 mg) | — | — |

Example 17

Further Sugar Alcohol Particles Used as Raw Materials

The following raw material grades were used in the examples in order to evaluate sensorial benefits:
Non-DC Xylitol: Xivia C from Dupont
Non-granulated Sorbitol—C*PharmSorbidex P 16656 from Cargill
Non-granulated Sorbitol—C*Sorbidex™ S 16607 from Cargill
Non-DC Isomalt: Isomalt GS from Beneo Paltinit
DC Mannitol: Pearlitol Flash from Roquette
Non-DC Erythritol: Zerose 16952 from Cargill
DC Erythritol—Zerose 16966 from Cargill
DC Xylitol—Xylitab 200 from Dupont
DC Isomalt—Isomalt DC 101 from Beneo Paltinit
DC Mannitol—Pearlitol 250SD from Roquette
DC Maltitol—Sweetpearl 300 DC from Roquette
DC Maltitol—Sweetpearl 200 DC from Roquette
DC Isomalt—galenIQ™ 720 from Beneo Paltinit
Non-DC Erythritol—ERYLITE® Erythritol from Jungbunzlauer
Non-DC Erythritol—Zerose™ 16961 from Cargill Example 18

Active Ingredients Delivered to the Oral Mucosa

A test panel of 8 test persons has been used for this test. Test subject abstain from eating and drinking at least 30 minutes before initiation of any test. Immediately before introducing of the powder delivery system into the oral cavity, the test subject swallows. The test subject refrains from chewing and swallowing during the test. After introducing the powder delivery system into the oral cavity, the test subjects let the powder dissolve for 10 seconds without moving it around. Then, saliva and any remains of the powder delivery system is moved around in the mouth without chewing and after 1 minute after starting the test, the test subject discards saliva including any powder delivery system fragments into a plastic cup, which is weighted. The test is repeated with a new powder delivery system under the same conditions as for the 1 minute test but instead of discarding saliva after 1 minute, the saliva is moved around and kept for 3 minutes in the mouth without swallowing before the test subject discards saliva including any powder delivery system fragments into a plastic cup, which is weighted. The saliva samples collected were analyzed for content of active ingredient. The saliva was positioned in a flask and weighted. Subsequently, a solvent was added for dissolution and dilution purposes. The solution was injected directly into an HPLC system and analyzed by an assay method by a HPLC method. The saliva were subject to 3 triple measurements for each of the 8 test persons, giving a total of 24 measurement for each sample. An average of the 24 measurements was calculated. By comparing the amount of active ingredient released (100%), and the amount of active ingredient in the saliva, the amount of active ingredient delivered to the oral mucosa could be estimated.

Example 18A

Hausner Ratio of Powders

In the following test example, the Hausner ratio was measured on example blends. The Hausner ratio is known by a person skilled in the art to be the ratio between stamped powder (g/mL) and unstamped powder (g/mL) according to known methods. The ratio expresses the ratio between the bulk density of the stamped and unstamped powder. The Hausner ratio is usually categorized according to a compressibility index and expresses the flow character of a powder. Best flow character is obtained with a Hausner ratio of 1.00 and the higher the Hausner ratio, the less flowing is the powder.

Various types of three sugar alcohol particles from Examples 2-7 were mixed in a 1:1 or 1:1:1 weight ratio. The three types of sugar alcohol particles were mixed according to the following procedure: An exact and equal amount of each type of sugar alcohol particles was measured by weight (between 3-5 g of each). The types of sugar alcohol particles were combined in a 70×100 mm plastic bag at ambient conditions and the content in the bag was mixed thoroughly. The powder delivery system were included in a flow-pack according to Example 8.

TABLE 14B

Different combinations of sugar alcohol particles.

| | | Combination of samples | | | Result |
|---|---|---|---|---|---|
| No. | Examples | Sample no. | Sample no. | Sample no. | ratio |
| 101 | 2 + 7 | 1 | 38 | — | 1.17 |
| 101* | 2 + 7 | 1 | 38 | — | 1.17 |
| 112 | 2 + 5 + 7 | 1 | 29 | 38 | 1.45 |
| 112** | 2 + 5 + 7 | 1 | 29 | 38 | 1.15 |
| 112* | 2 + 5 + 7 | 1 | 29 | 38 | 1.30 |

*CaCO3 added in 5% by weight.
**SiO2 in 2% by weight.

Example 18B

Swishing Time Measurements (Dissolution)

In the following test example, time measurements were evaluated on the samples provided in the previous examples following the method of 1) providing a powder mixture as outlined in the samples above, 2) allowing the powder samples to dissolve after oral administration by means of the oral saliva generated, 3) swishing the fluid generated comprising the dissolved powder mixture in the oral cavity.

TABLE 14C

Different combinations of sugar alcohol particles.

| | | Combination of samples | | | Result |
|---|---|---|---|---|---|
| No. | Examples | Sample no. | Sample no. | Sample no. | Dissolution (s) |
| 101 | 2 + 7 | 1 | 38 | — | <10 s |
| 101* | 2 + 7 | 1 | 38 | — | <10 s |
| 112 | 2 + 5 + 7 | 1 | 29 | 38 | <10 s |
| 112** | 2 + 5 + 7 | 1 | 29 | 38 | <10 s |
| 112* | 2 + 5 + 7 | 1 | 29 | 38 | <10 s |

*CaCO3 added in 5% by weight.
**SiO2 in 2% by weight. Evaluation of time until the powder mixture is dissolved. Dissolution in seconds. Swishing was conducted by forcing the saliva generated around in the oral cavity.

The result was highly surprising since it was not expected that the powder mixture according to the invention was able to generate adequate saliva and to dissolve as quickly as was seen. The method of the invention shows that the powder mixture was able to resemble a liquid mouthwash without adding water but solely by virtue of the saliva generated upon and after oral administration.

Example 18C

Swishing Time Measurements (Saliva Generation)

In the following test example, time measurements were evaluated on the samples provided in the previous examples following the method of 1) providing a powder mixture as outlined in the samples above, 2) allowing the powder samples to dissolve after oral administration by means of the oral saliva generated, 3) swishing the fluid generated comprising the dissolved powder mixture in the oral cavity.

TABLE 14D

Different combinations of sugar alcohol particles.

| | | Combination of samples | | | Result Fluid |
|---|---|---|---|---|---|
| No. | Examples | Sample no. | Sample no. | Sample no. | (ml) |
| 101 | 2 + 7 | 1 | 38 | — | >1.0 ml |
| 101* | 2 + 7 | 1 | 38 | — | >1.0 ml |
| 112 | 2 + 5 + 7 | 1 | 29 | 38 | >2.0 ml |
| 112** | 2 + 5 + 7 | 1 | 29 | 38 | >2.0 ml |
| 112* | 2 + 5 + 7 | 1 | 29 | 38 | >2.0 ml |

*CaCO3 added in 5% by weight.
**SiO2 in 2% by weight. Evaluation of the total content of saliva/fliud generated from oral administration until 30 seconds after administration. Swishing was conducted by forcing the saliva generated around in the oral cavity.

The result was highly surprising since it was not expected that the powder mixture according to the invention was able to generate such a high amount of saliva. The method of the invention shows that the powder mixture was able to resemble a liquid mouthwash without adding water but solely by virtue of the saliva generated upon and after oral administration.

Example 18D

Swishing Time Measurements (Cooling Sensation)

In the following test example, time measurements were evaluated on the samples provided in the previous examples following the method of 1) providing a powder mixture as outlined in the samples above, 2) allowing the powder samples to dissolve after oral administration by means of the oral saliva generated, 3) swishing the fluid generated comprising the dissolved powder mixture in the oral cavity.

TABLE 14E

Different combinations of sugar alcohol particles.

| | | Combination of samples | | | Result Scale |
|---|---|---|---|---|---|
| No. | Examples | Sample no. | Sample no. | Sample no. | 1-5 |
| 101 | 2 + 7 | 1 | 38 | — | 5 |
| 101* | 2 + 7 | 1 | 38 | — | 5 |
| 112 | 2 + 5 + 7 | 1 | 29 | 38 | 5 |
| 112** | 2 + 5 + 7 | 1 | 29 | 38 | 5 |
| 112* | 2 + 5 + 7 | 1 | 29 | 38 | 5 |

*CaCO3 added in 5% by weight.
**SiO2 in 2% by weight. Evaluation of the sensation of cooling from oral administration until 30 seconds after administration in a scale from 1-5 with 5 as the highest sensation of cooling. Swishing was conducted by forcing the saliva generated around in the oral cavity.

The result was highly surprising since it was not expected that the powder mixture according to the invention was able to generate a sensation of cooling to a degree experienced. The method of the invention shows that the powder mixture was able to resemble a liquid mouthwash without adding water but solely by virtue of the saliva generated upon and after oral administration and was able to provide a distinct cooling sensation.

Example 19

Sensorial Evaluation Test Set-Up

Sensorial tests were performed on all examples to reveal very important characteristics and properties of the powder delivery system. These sensorial parameters are important as indicators of the structure of the powder delivery system composition. The structure is the underlying guidance as to how the powder delivery system resembles the structure of a comparative powder delivery system, which is used as a reference in the test series, i.e. the powder delivery systems are compared to each other in the test series of preferably 5 samples. The test set-up was composed of 8 test persons in a test panel. Each of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent compared to the reference sample. The reference sample is given the rating "++" for all the parameters, i.e. "+++++" means that the powder delivery system was far better than the reference and "+" means that the powder delivery system was inferior to the reference. "0" indicated that it was not tested.

Six different parameters were tested in a test panel:

| Mouthfeel | Melting | Flavor | Off-notes | Salivation | Cooling |
| --- | --- | --- | --- | --- | --- |

"Mouthfeel"—the general impression of the powder delivery system when placed in the mouth with respect to elements such as roughness, texture and a sandy or dusty feeling.

"Melting"—the impression of the powder delivery system when placed in the mouth. For instance, a feeling that the powder delivery system melts on the tongue with a resulting sticking feeling gave a low rating, whereas a less sticky experience gave a higher rating. A slow melting powder deliver system gave a low rating, whereas a fast meting give a high rating.

"Flavor"—the overall impression of the powder delivery system with respect to flavor including the sweetness profile. For instance, a very low flavor experience gave a very low rating and a too high flavor also gave a very low rating.

"Off-notes"—the overall impression of the off-note from the active ingredients in the composition. For instance, if off-notes (grass, bitter notes, irritation in the throat) were experienced in the throat, a low rating was given and if other uncomfortable sensations was experienced, a low rating was also given.

"Salivation"—the overall impression of the watering effect.

"Cooling"—the overall impression of cooling.

Example 20

Sensorics Evaluation of Sensorial Parameters

TABLE 15

Evaluation in accordance with Example 19.

| Sample no. | Mouthfeel | Melting | Flavor | Salivation | Cooling |
| --- | --- | --- | --- | --- | --- |
| (Isomalt GS + mannitol)* | ++ | ++ | ++ | ++ | ++ |
| (Xivia C + sorbitol)** | ++ | ++ | +++++ | +++ | ++++ |
| 91 | ++++ | +++++ | +++++ | +++++ | +++++ |
| 94 | ++++ | ++++ | +++ | +++ | ++ |
| 95 | +++ | ++++ | ++++ | +++++ | +++ |

TABLE 15-continued

Evaluation in accordance with Example 19.

| Sample no. | Mouthfeel | Melting | Flavor | Salivation | Cooling |
| --- | --- | --- | --- | --- | --- |
| 96 | +++++ | +++++ | +++ | +++ | +++ |
| 101 | +++++ | +++++ | +++++ | ++++ | +++++ |
| 102 | +++ | ++++ | +++ | ++ | ++ |
| 103 | +++ | +++ | +++ | ++ | +++ |
| 112 | +++++ | +++++ | +++++ | +++++ | +++++ |
| 113 | +++ | +++ | +++ | ++++ | +++ |
| 114 | +++ | ++++ | ++++ | +++ | +++ |
| 115 | ++ | ++ | ++++ | ++++ | ++++ |
| 116 | ++++ | +++++ | ++++ | +++ | ++++ |
| 117 | ++++ | +++++ | +++++ | ++++ | +++++ |

*comparative 1.
**comparative 2.

The results of the samples above correspond to an illustration of selected samples that were tested with respect to sensorial evaluation according to the set up in Example 19. The additional samples provided in the previous examples were also tested in the same way with respect to the same parameters, and the results were in the same way considered to be advantageous.

In particular, it was seen that the salivation effect was especially pronounced for non-DC sugar alcohol particles with more than 50% of the particles being below 250 microns in combination with further particles when at least 20% by the powder mixture contained these non-DC sugar alcohol particles.

Additionally, it was seen that the cooling effect was especially pronounced for DC sugar alcohol particles that have not been granulated and having more than 50% of the particles being below 250 microns in combination with further particles when at least 20% by the powder mixture contained these DC sugar alcohol particles that have not been granulated.

Example 21

Evaluation of Sensorial Experience

TABLE 16

Evaluation of mouthfeel and other sensorial properties.

| Sample no. | Mouthfeel (Good/Acceptable (Acc)/Poor) | Sensorial experience |
| --- | --- | --- |
| 122 | Good | Pleasant mouthfeel with a sweet and pure mint flavor. |
| 126 | Good | Pleasant mouthfeel with a sweet and candy-like raspberry flavor. |
| 127 | Good | Pleasant mouthfeel with a soft and full eucalyptus flavor. |
| 128 | Good | Pleasant mouthfeel with a sweet and pleasant orange flavor. |
| 129 | Good | Pleasant mouthfeel with a sweet and clear coffee flavor. |
| 132 | Good | Pleasant mouthfeel with a soft fizziness and a fresh acerbic taste. |
| 141 | Good | Pleasant mouthfeel with a very full elderberry taste. |
| 142 | Acc. | Dry mouthfeel at first, but fast salivation relieves this partly. A little dry aftertaste, but acceptable according to the amount of zinc. |
| 152 | Good | Pleasant mouthfeel with good sweetness profile and fast melting. |
| 162 | Acc. | A good mouthfeel, but a slightly bitter taste. |

The results of the samples above correspond to an illustration of selected samples that were tested with respect to sensorial experience. The additional samples provided in the previous examples were also tested in the same way with respect to mouth feel and sensorial experience, and the results were in the same way considered to be advantageous.

In particular, it was seen that an advantageous mouth feel and sensorial experience was especially pronounced for non-DC sugar alcohol particles with more than 50% of the particles being below 250 microns in combination with further particles when at least 20% by the powder mixture contained these non-DC sugar alcohol particles.

Additionally, it was seen that an advantageous mouth feel and sensorial experience was especially pronounced for DC sugar alcohol particles that have not been granulated and having more than 50% of the particles being below 250 microns in combination with further particles when at least 20% by the powder mixture contained these DC sugar alcohol particles that have not been granulated.

The invention claimed is:

1. A method of achieving oral care benefits, comprising the steps of:
   a) providing a swishable powder delivery system having a content of at least two types of sugar alcohol particles with different particle size distributions and one or more active ingredients, the powder delivery system being a dry and flowable population of particles in solid form;
   b) administering said dry and flowable population of particles in solid form without adding water to the oral cavity of a human subject;
   c) swishing said dry and flowable population of particles in solid form without adding water by the human subject; and
   wherein fluid is generated in the oral cavity upon swishing said dry and flowable population of particles in solid form without adding water by the human subject, thereby resembling a liquid mouthwash.

2. The method according to claim 1, wherein swishing said powder delivery system is characterised by forcing the powder delivery system around the oral cavity for at least 5 seconds.

3. The method according to claim 1, wherein at least a portion of the fluid generated by swishing said powder delivery system is forced around the oral cavity for at least 10 seconds.

4. The method according to claim 1, wherein oral care benefits are obtained by swishing said powder delivery system and/or at least a portion of the fluid generated in the oral cavity for at least 10 seconds.

5. The method according to claim 1, wherein at least one of the at least two types of sugar alcohol particles with different particle size distributions is substantially free-flowing.

6. The method according to claim 1, wherein the Hausner ratio of the powder delivery system is between 1.00 and 1.59.

7. The method according to claim 1, wherein the powder delivery system provides an improved cooling effect compared to a powder delivery system without at least one of the at least two types of sugar alcohol particles with different particle size distributions.

8. The method according to claim 1, wherein the powder delivery system provides an improved watering effect compared to a powder delivery system without at least one of the at least two types of sugar alcohol particles with different particle size distributions.

9. The method according to claim 1, wherein the powder delivery system provides an improved mouthfeel compared to a powder delivery system without at least one of the at least two types of sugar alcohol particles with different particle size distributions, the improved mouthfeel including at least one of less sandy mouthfeel, less dusty mouthfeel, less roughness mouthfeel, less sticky or improved texture.

10. The method according to claim 1, wherein the population of particles includes at least 20% of one type of sugar alcohol particles having a particle size with more than 80% of the particles being below 250 microns and at least 20% of another type of sugar alcohol particles having a particle size with more than 80% of the particles being below 250 microns.

11. The method according to claim 1, wherein the population of particles includes at least 20% of one type of sugar alcohol particles having a particle size with more than 80% of the particles being below 250 microns and at least 20% of another type of sugar alcohol particles having a particle size with more than 80% of the particles being below 300 microns.

12. The method according to claim 1, wherein the population of particles includes at least two types of sugar alcohol particles comprising i) granulated sugar alcohol particles and ii) non-directly compressible (non-DC) sugar alcohol particles.

13. The method according to claim 1, wherein the population of particles includes at least two types of sugar alcohol particles comprising i) granulated sugar alcohol particles and iii) directly compressible (DC) sugar alcohol particles that are not granulated sugar alcohol particles.

14. The method according to claim 1, wherein the population of particles includes at least two types of sugar alcohol particles comprising ii) non-directly compressible (non-DC) sugar alcohol particles and iii) directly compressible (DC) sugar alcohol particles that are not granulated sugar alcohol particles.

15. The method according to claim 1, wherein the population of particles includes at least two types of sugar alcohol particles comprising ii) non-directly compressible (non-DC) sugar alcohol particles in an amount of at least 20% by weight of the population of particles and iii) directly compressible (DC) sugar alcohol particles that are not granulated sugar alcohol particles in an amount of at least 20% by weight of the population of particles.

16. The method according to claim 1, wherein the population of particles includes at least two types of sugar alcohol particles comprising ii) non-directly compressible (non-DC) sugar alcohol particles having a particle size with more than 80% of the particles being below 500 microns and iii) directly compressible (DC) sugar alcohol particles that are not granulated sugar alcohol particles having a particle size with more than 80% of the particles being below 500 microns.

17. The method according to claim 1, wherein the population of particles includes at least two types of sugar alcohol particles comprising ii) non-directly compressible (non-DC) sugar alcohol particles having a particle size with more than 50% of the particles being below 250 microns and iii) directly compressible (DC) sugar alcohol particles that are not granulated sugar alcohol particles having a particle size with more than 80% of the particles being below 300 microns.

18. The method according to claim 1, wherein the population of particles includes at least three types of sugar alcohol particles comprising i) granulated sugar alcohol particles, ii) non-directly compressible (non-DC) sugar alcohol particles and ili) directly compressible (DC) sugar alcohol particles that are not granulated sugar alcohol particles.

19. The method according to claim 1, wherein the population of particles includes at least two types of sugar alcohol particles comprising i) granulated sugar alcohol particles selected from granulated particles of xylitol, maltitol, isomalt, mannitol, erythritol, lactitol or combinations thereof.

20. The method according to claim 1, wherein the population of particles includes at least two types of sugar alcohol particles comprising ii) non-directly compressible (non-DC) sugar alcohol particles selected from non-DC particles of xylitol, maltitol, isomalt, mannitol, erythritol, lactitol or combinations thereof.

21. The method according to claim 1, wherein the population of particles includes at least two types of sugar alcohol particles comprising iii) directly compressible (DC) sugar alcohol particles that are not granulated sugar alcohol particles, and wherein the directly compressible (DC) sugar alcohol particles that are not granulated sugar alcohol particles iii) comprise sorbitol.

22. The method according to claim 1, wherein the population of particles includes at least two types of sugar alcohol particles comprising i) granulated sugar alcohol particles and ii) non-directly compressible (non-DC) sugar alcohol particles in a weight ratio between i) and ii) of between 0.2 and 5.

23. The method according to claim 1, wherein the population of particles includes at least two types of sugar alcohol particles comprising i) granulated sugar alcohol particles and iii) directly compressible (DC) sugar alcohol particles that are not granulated sugar alcohol particles in a weight ratio between i) and iii) of between 0.2 and 5.

24. The method according to claim 1, wherein the population of particles includes at least two types of sugar alcohol particles comprising ii) non-directly compressible (non-DC) sugar alcohol particles and iii) directly compressible (DC) sugar alcohol particles that are not granulated sugar alcohol particles in a weight ratio between ii) and iii) of between 0.2 and 5.

25. The method according to claim 1, wherein the active ingredient comprises oral care agents including zinc acetate and/or zinc gluconate.

26. The method according to claim 1, wherein the active ingredient comprises oral care agents for oral care benefits including bad breath, plaque, gingivitis, whitening, or combinations of two or more thereof.

27. The method according to claim 1, wherein the active ingredient comprises anti-septics including cetyl pyridinium chloride (CPC) and/or essential oils selected from the group consisting of cineole, menthol, methyl salicylate, thymol, and any combination thereof.

28. The method according to claim 1, wherein the swishable powder further comprises abrasive agents, including calcium carbonate and/or talc.

29. The method according to claim 1, wherein the swishable powder further comprises flow promoting agents, including silicon dioxide and/or rice hulles and/or cellulosic fibers.

* * * * *